(12) United States Patent
Romaine et al.

(10) Patent No.: US 8,686,218 B2
(45) Date of Patent: Apr. 1, 2014

(54) STRATEGIES FOR THE TRANSGENIC MANIPULATION OF FILAMENTOUS FUNGI

(75) Inventors: C. Peter Romaine, State College, PA (US); Carl David Schlagnhaufer, Julian, PA (US); Benjamin Michael Woolston, Long Valley, NJ (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 13/640,131

(22) PCT Filed: Apr. 12, 2011

(86) PCT No.: PCT/US2011/032087
§ 371 (c)(1),
(2), (4) Date: Oct. 9, 2012

(87) PCT Pub. No.: WO2011/130247
PCT Pub. Date: Oct. 20, 2011

(65) Prior Publication Data
US 2013/0276168 A1    Oct. 17, 2013

Related U.S. Application Data

(60) Provisional application No. 61/342,429, filed on Apr. 14, 2010.

(51) Int. Cl.
*C12Q 1/68* (2006.01)
(52) U.S. Cl.
USPC ............ 800/260; 435/6.1; 435/69.1; 435/484
(58) Field of Classification Search
None
See application file for complete search history.

(56) References Cited

U.S. PATENT DOCUMENTS

| | | | |
|---|---|---|---|
| 5,674,707 A | 10/1997 | Hintz et al. | |
| 6,551,797 B1 * | 4/2003 | Pfaller et al. | 435/69.1 |
| 2002/0016982 A1 | 2/2002 | Romaine et al. | |
| 2006/0073560 A1 | 4/2006 | Burton et al. | |
| 2009/0170807 A1 * | 7/2009 | Quanz | 514/54 |

FOREIGN PATENT DOCUMENTS

| | | |
|---|---|---|
| CN | 88 1 01628 A | 10/1988 |
| CN | 1376778 A | 10/2002 |
| CN | 1521256 A | 8/2004 |
| WO | WO 95/02691 A2 | 1/1995 |

OTHER PUBLICATIONS

The Penn State Research Foundation et al., PCT/US2011/032087, filed Apr. 14, 2011, "International Search Report" mailed Jan. 2, 2012, 4 pages.
The Penn State Research Foundation, PCTUS2011032087, "Supplementary European Search Report", Date completed Aug. 14, 2013.
Kassim, M.Y., et al., "Effects of Casing Soil Amendments and Nutrient Supplementation on Mushroom Cropping", J. King Saud Univ., vol. 2, Agric. Sci. (2), pp. 225-230, (1990).
Markham, Paul, "Occusions of septal pores in filamentous fungi", Mycol. Res. 98 (10): 1089-1106 (1994).
Zied, Diego Cunha, "A Study of Compost Added to a Casing Technique in *Agaricus bisporus* Cultivation from Phase III Bulk Compost", HortScience vol. 45 (11), Nov. 2010, pp. 1649-1653.
Falconer, Ruth E. et al, "Biomass recycling and the origin of phenotype in fungal mycelia", Proceedings of the Royal Society B (2005) 272, pp. 1727-1734.
Lacourt, Isabelle, et al., "Isolation and Characterization of Differentially Expressed Genes in the Mycelium and Fruit Body of Tuber Borchii", Applied and Environmental Microbiology, Sep. 2002, pp. 4574-4582.
Levin, Ana M., et al., "Spatial Differentiation in the Vegetative Mycelium of Aspergillus niger", Eukaryotic Cell, Dec. 2007, pp. 2311-2322.
CN 1376778-English. (2002).
CN 1521256-English. (2004).
Taiwan Search Report, date of completion of search: Sep. 2, 2013, pp. 12-13.

* cited by examiner

*Primary Examiner* — Jim Ketter
(74) *Attorney, Agent, or Firm* — McKee, Voorhees & Sease, P.L.C.

(57) ABSTRACT

Disclosed is a new technology that enables the transgenic modification of a mushroom-forming fungus to confer a transgenic genotype and/or phenotype. According to the invention herein, one can manipulate the fruiting body of a fungus conferring an altered phenotype, but a wild-type genotype. The fruiting body itself is devoid of any cognate transgene, and Applicants have discovered a new mechanism of protein synthesis and accumulation in fungi and a technique to independently control the genotype and phenotype of the fruiting body.

26 Claims, 15 Drawing Sheets

| | HGS/HGS | HGS/WT | GGS/GGS | GGS/WT | LGS/LGS | LGS/WT |
|---|---|---|---|---|---|---|
| First-harvest Fruiting Bodies | | | | | | |
| Histological GUS Assay | | | | | | |
| Quantitative GUS Assay | 1.45 (100%) | 0.91 (63%) | 0.55 (100%) | 0 (0%) | 6.56 (100%) | 0 (0%) |
| qPCR Analysis | 4,653±81 (100%) | 2,275±364 (49%) | 8,753±547 (100%) | 6,370±44 (77%) | 19,534±78 (100%) | 9,334±491 (48%) |

SEQUENCE LISTING

```
<160> NUMBER OF SEQ ID NOS: 14

<210> SEQ ID NO 1
<211> LENGTH: 22
<212> TYPE: DNA
<213> ORGANISM: Agaricus bisporus

<400> SEQUENCE: 1
cgtgacaaga accatccaag cg                                              22

<210> SEQ ID NO 2
<211> LENGTH: 22
<212> TYPE: DNA
<213> ORGANISM: Agaricus bisporus

<400> SEQUENCE: 2
gggtagccat cacaaacagc ac                                              22

<210> SEQ ID NO 3
<211> LENGTH: 27
<212> TYPE: DNA
<213> ORGANISM: Agarisuc bisporus

<400> SEQUENCE: 3
cgaactagtc tgtacccgat caacacc                                         27

<210> SEQ ID NO 4
<211> LENGTH: 22
<212> TYPE: DNA
<213> ORGANISM: Agaricus bisporus

<400> SEQUENCE: 4
tccgcacgcc gaacggctct tc                                              22

<210> SEQ ID NO 5
<211> LENGTH: 21
<212> TYPE: DNA
<213> ORGANISM: Agaricus bisporus

<400> SEQUENCE: 5
cgacgggtgt gaacgcaaag g                                               21

<210> SEQ ID NO 6
<211> LENGTH: 22
<212> TYPE: DNA
<213> ORGANISM: Agaricus bisporus

<400> SEQUENCE: 6
caatcagtcg atcaacgttc gc                                              22
```

```
<210> SEQ ID NO 7
<211> LENGTH: 20
<212> TYPE: DNA
<213> ORGANISM: Agaricus bisporus

<400> SEQUENCE: 7
ggaagtttag atagggggacc                                                    20

<210> SEQ ID NO 8
<211> LENGTH: 20
<212> TYPE: DNA
<213> ORGANISM: Agaricus bisporus

<400> SEQUENCE: 8
gtggctgtct gaaaagatac                                                     20

<210> SEQ ID NO 9
<211> LENGTH: 19
<212> TYPE: DNA
<213> ORGANISM: Agaricus bisporus

<400> SEQUENCE: 9
cgacggactg accatcgat                                                      19

<210> SEQ ID NO 10
<211> LENGTH: 21
<212> TYPE: DNA
<213> ORGANISM: Agaricus bisporus

<400> SEQUENCE: 10
gaacttgccg tcgttgactt c                                                   21

<210> SEQ ID NO 11
<211> LENGTH: 18
<212> TYPE: DNA
<213> ORGANISM: Agaricus bisporus

<400> SEQUENCE: 11
ccgttcggcg tgcggacc                                                       18

<210> SEQ ID NO 12
<211> LENGTH: 19
<212> TYPE: DNA
<213> ORGANISM: Agaricus bisporus

<400> SEQUENCE: 12
atgctcctcg tgccgtctt                                                      19

<210> SEQ ID NO 13
<211> LENGTH: 19
<212> TYPE: DNA
<213> ORGANISM: Agaricus bisporus

<400> SEQUENCE: 13
tgccccatac caaccatca                                                      19

<210> SEQ ID NO 14
<211> LENGTH: 23
<212> TYPE: DNA
<213> ORGANISM: Agaricus bisporus

<400> SEQUENCE: 14
ccttccatcg tcggtcgtcc tcg                                                 23
```

STRATEGIES FOR THE TRANSGENIC MANIPULATION OF FILAMENTOUS FUNGI

CROSS-REFERENCE TO RELATED APPLICATIONS

This is a National Phase application claiming priority to PCT/US2011/032087 filed Apr. 12, 2011 which claims priority under 35 U.S.C. §119 to provisional application U.S. Ser. No. 61/342,429 filed Apr. 14, 2010, all of which are herein incorporated by reference in their entireties.

GRANT REFERENCE

This invention was made with government support under Hatch Act Project No. PEN04096, awarded by the United States Department of Agriculture and under Contract No. HR0011-07-9-0004, awarded by DARPA, The government has certain rights in the invention.

FIELD OF THE INVENTION

This invention relates generally to the field of molecular biology. More specifically, this invention relates to the characterization of novel methods for the transgenic manipulation of fungi. The methods of the invention can be used to improve fungal species by recombinant technologies known to those of skill in the art, such as the manipulation for increased pathogen, pest, and pesticide resistance, and yield and quality, extended produce shelf life, improved culinary, nutritional, and medicinal value, and the like, as well as for commercial production of heterologous (and homologous) proteins.

BACKGROUND OF THE INVENTION

Fungi are microscopic, spore-bearing organisms that lack chlorophyll and therefore derive nourishment from dead or living organic matter. Introductory Mycology (eds.). Alexopoulos, C. J., Mims, C. W., and Blackwell, M. (1996). $4^{th}$ edition. Chapter 1. Because they share characteristics of both plants and animals, they are classified separately in the kingdom Fungi. Within this kingdom, there are the "filamentous fungi", so named because their vegetative bodies consist of small thread-like filaments referred to as "hyphae". Typically, the hyphae grow in a branching fashion, spreading over or within the substrate used as a source of nourishment, thereby forming a network of hyphae called "mycelium". Thus, the mycelium is the vegetative body of the fungus. In the life cycle of most filamentous fungi, the vegetative mycelium gives rise to either asexual or sexual spores. Asexual spores are referred to by a variety of names, but commonly used terms are "conidia", "condiospores", or simply "spores". The vegetative mycelium of the fungus may differentiate, with the appropriate biological and environmental cues, into a sexual reproductive spore-bearing structure. Some fungi produce sizable, fibrous ("fleshy"), spore-bearing reproductive structures variously called "mushrooms" "fruit bodies" "basidiocarps", "ascocarps", "conks", or "basidomes". The fruit bodies of some fungi are edible; being valued for their culinary, nutritional, or medicinal qualities, and, as such, are highly sought after or grown commercially.

The fruit body may be differentiated into specialized tissues such as the fleshy umbrella-shaped cap (pileus), stem (stipe), cup at the base of the stem (volva), and gills (lamallae) bearing the sexual spores. A thin tissue known as the veil (velium) may cover the underside of the cap. The veil ruptures as the fruit body approaches maturity, exposing the gills and permitting the discharge of the sexual spores into the environment. However, the fruit bodies of some fungi lack gills all together, and instead are composed of fleshy tissue perforated with small pores or locules bearing the sexual spores. Sexual spores produced by the fleshy reproductive structures of fungi are described by numerous terms, as for example, "ascospores", "basidiospores", or simply "spores".

Thus, the fruit body of fungi is functionally comparable to the reproductive structure of plants known as the flower, whereas both asexual and sexual spores are comparable to the seed of plants, being important in the dispersal and survival of the fungus in nature. Under suitable environmental conditions, the spore germinates to form another generation of vegetative hyphae and so completing the life cycle of the fungus.

Filamentous fungi have a vital role as one of the primary decomposers within their varied natural habitats. They also have a large impact on food production. Some fungi, such as mushrooms, are used as food, while others are plant pathogens that are responsible for devastating crop losses all over the world. Filamentous fungi are also important in industry and medicine as they secret a diverse array of enzymes (e.g. proteases, lipases) as well as primary (e.g. organic acids) and secondary metabolites (e.g. antibiotics penicillin and cephalosporin). The cultivated mushroom *Agaricus bisporus* is a significant crop, with a world-wide production in 1990 of 1.5 million tons. Filamentous fungi are also attractive as hosts for large-scale production of both homologous and heterologous proteins, because they have the capacity to secrete substantial amounts of proteins.

About 40% of the commercially available enzymes are derived from filamentous fungi. Lowe, Handbook of Applied Mycology. Fungal Biotechnology (eds.) Arora, D. K. Elander, R. P. & Mukerji, K. G. 681-708 (Marcel Dekker, New York; 1992). These enzymes are usually produced by species of the genera *Aspergillus* and *Trichoderma*. Because they secrete large amounts of protein into the medium, they can be grown in large-scale fermentation, and they are generally accepted as safe for the food industry.

General problems associated with the commercial cultivation of mushrooms (*A. bisporus*) include diseases caused by pathogens like *Verticillium fungicola* (dry bubble), *Trichoderma harzianum* biotypes 2 and 4 (green mold), *Pseudomonas tolaasii* (blotch), and dsRNA viruses (La France isolate and MVX), the major insect pest [sciarid fly (*Lycoriella mali*)], an extremely short shelf life of the product related to bacterial spoilage and rapid senescence, and browning (bruising) of the fruit body associated with the action of endogenous poly-phenoloxidases (PPO, like tyrosinase). To further improve product quality, conventional breeding programs for *A. bisporus* have been only moderately successful and may not be sufficient in the long term. This is because conventional breeding techniques for fungi are highly time consuming, and because the genetic variation in commercially available strains is limited, offering little advancement by selection (Horgen et al. "Homology between mitochondrial DNA of *Agaricus bisporus* and an internal portion of a linear mitochondrial plasmid of *Agaricus bitorquis*" Curr Genet. 1991 June; 19:495-502.

In the case of *A. bisporus*, the main problem for effective breeding strategies is caused by the rather abnormal life-cycle involving the unusual simultaneous segregation of either parental nucleus into one basidiospore. After outgrowth of this basidiospore, heterokaryotic mycelium is formed containing nuclei and genetic characteristics that do not differ from those present in the parental mycelium. In addition, only little recombinational activity is observed during meiosis (Summerbell et al. 1989. Genetics 123: 293-300).

For this reason, investigators all over the world have attempted to develop a transformation system for commercial mushrooms, such as *A. bisporus*, for the introduction of novel characteristics. For other fungi, as well as plants, animals, and bacteria, the application of gene transfer technology is quite common and has already resulted in commercial application. However, the absence of an efficient, reproducible, stable transformation system generally applicable in a wild-type background in many fungi has strongly hampered molecular-biological research on such organisms.

Current transformation techniques for fungi have included a combination of $CaCl_2$ and polyethylene glycol (PEG), electroporation, and particle bombardment to introduce DNA into protoplasts, mycelium, or spores. These have been either without success, or not reproducible. The lack of a practical gene transfer system is the single largest obstacle precluding the use of molecular approaches for the genetic improvement of mushrooms. Despite considerable interest in the development of a transformation scheme, no method is in general use today, due to low efficiency or lack of utility and convenience.

In recent approaches, several fungi, including *A. bisporus*, have been transformed using an *Agrobacterium*-based transformation system. Although these methods are more convenient than the existing protoplast-based schemes, they have thus far suffered from a comparably low efficiency of transformation using complicated systems.

For example, Gouka et. al. describe a transformation procedure for targeted homologous recombinations in fungi, (Gouka et. al. Nature Biotechnology Vol 17 Jun. 1999, "Transformation of *Aspergillus awamori* by *Agrobacterium tumefaciens*-mediated homologous recombination" pp 598-601). According to this procedure a specifically engineered *A. awamori* recipient strain containing a 3'-deleted nonfunctional pyrG gene and an *Agrobacterium* strain containing a binary vector suitable for restoring the pyrG gene by recombination are used. Homologous recombination between the repair construct and the recipient host result in restoration of functional pyrG gene and integration of the vector at the pyrG locus. The paper reported a high of 150 transformants per $10^7$ conidia.

De Groot et. al report yet another *Agrobacterium*-based method of transforming filamentous fungi, (De Groot et. el. Nature Biotechnology Vol 16 Sep. 1998, "*Agrobacterium tumefaciens*-mediated transformation of filamentous fungi" pp. 839-842). This paper investigated the ability of *Agrobacterium* to transfer T-DNA to the *A. awamori* protoplasts (vegetative cells with the cell walls removed) and conidia. The transformation frequency varied from approximately 300 to 7200 transformants per $10^7$ protoplasts, which was up to 600 times higher than PEG transformation rates. When conidia were used, the transformation frequency varied from 1000 to 9000 transformants per $10^7$ conidia. Vegetative mycelial tissue was also used.

Other fungi transformation schemes are disclosed in WO95/02691 and WO98/45455. All of these have focused on transformation using protoplasts, spores, and vegetative mycelium as the recipient tissue.

Numerous scientists are using the Penn State genetic transformation methodology in their research efforts. There are a growing number of examples in the literature where the methodology has enabled the expression of recombinant proteins and RNA transcripts (i.e. hairpin RNA-induced RNAi) in *A. bisporus*. In each case, a traditional approach was taken in which the transgene construct entailing a nucleotide sequence-of-interest joined to an operable promoter and terminator was stably integrated in the *Agaricus* genome, resulting in a fruiting body having both a transgenic genotype and phenotype. An *A. bisporus* line generated in this manner currently has low commercial value, as genetically modified mushrooms are currently not preferred in the marketplace. Further, if the objective is to utilize *A. bisporus* as a manufacturing platform, a traditional approach to genetic modification often fails to achieve high-level expression of the protein-of-interest. Therefore, there is a continual quest to identify new strategies for attaining higher levels of protein production.

As can be seen from the foregoing, there is a continuing need in the art for development of effective, convenient, and expeditious fungal transgenic protocols.

It is thus an object of the present invention to provide a transgenic manipulation system for fungi that will accomplish the foregoing need.

A further object of this invention is to provide mechanisms for application of transgenic techniques to increase yield, disease, and pest resistance, product quality, shelf life, or culinary, nutritional, or medicinal value, to produce commercially, or other such protocols.

It is yet another object of the invention to provide polynucleotide constructs, vectors, transformed cells for use in such transgenic manipulation protocols.

Other objects of the invention will become apparent from the description of the invention that follows.

SUMMARY OF THE INVENTION

The improved transformation method described herein provides a practical method for using transgenic technology in the genetic improvement of filamentous fungi, and represents an important tool for the molecular genetic analysis of biological processes in these organisms. Further, the method enables the genetic modification of fungi to serve as biofermentors for the mass-scale production of desired products, as for one example, industrial or therapeutic proteins. Additionally, the transgenic manipulation protocol, with modifications to the choice of promoter and strain of *Agrobacterium*, is applicable to all fungal species that bear fleshy fruit bodies, and may be optimized by selection of strain of *Agrobacterium* or promoter. Examples of filamentous fungi useful for the invention include members of the phyla Basidoiomycota and Ascomycota as follows: *Coprinus* spp., *Coriolus* spp., *Agaricus* spp. including the species bisporus, *Flammulina velutipes, Lentinula edodes, Morchella* spp., *Phanerochaete chrysosporium, Pleurotus ostreatus, Schizophyllum commune,* and *Tricholoma matsutake*, among others.

This new technology enables the transgenic modification of mushroom to confer a transgenic genotype and/or phenotype. In transgenic breeding of the mushroom as a food item one can manipulate the fruiting body of a fungus conferring an altered phenotype, but a wild-type genotype. The fruiting body itself is devoid of the cognate transgene, and Applicant's have discovered a new mechanism of protein synthesis and accumulation in fungi and a technique to independently control the genotype and phenotype of the fruiting body.

Applicants have surprisingly found that the genotype of the inoculant used in the upper water-holding substrate (such as peat) in a two layer system with a lower nutrient substrate determines the genotype of the fruiting body of the cultivated mushroom. Use of a transgenic inoculant gave rise to a transgenic fruiting body. According to the invention, the rate of this inoculant must be high enough to prevent the spawn inoculant in the lower compost substrate from growing thought the case layer and participating in the formation of a chimeric fruiting body. Applicant's have further found that the choice of promoter, a recombinant protein and/or RNA transcript expressed in the mycelium colonizing the lower compost substrate was translocated into the developing fruit body. Thus one may manipulate the phenotype and RNA and proteins expressed in the fruiting body to be different that the genotype of the same. This is the first long-distance transport of a protein and/or RNA transcript in fungi.

With the transgenic manipulation methods of the invention, genetic engineering techniques known in the art can be used to genetically and phenotypically manipulate filamentous fungi for ease of cultivation or production, improved culinary, medicinal, or nutritional value, or production of recombinant proteins for harvest. The invention further comprises novel compositions including protein products isolated from such transgenic fungi. Also included are expression constructs, for use in this procedure as well as transformed cells, vectors, and transgenic fungi incorporating the same.

Definitions

Various terms relating to the compositions and methods of the present invention are used herein above and also throughout the specification and claims and unless otherwise indicated shall have the meaning specified herein.

Various units, prefixes, and symbols may be denoted in their International System of Units accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5$^{th}$ edition, 1993). The terms defined below are more fully defined by reference to the specification as a whole.

As used herein the term "*Agrobacterium*" shall be intended to include any bacterial species and its conservatively modified variants that is capable of infecting a desired fungal cell. The *A. tumefaciens* Ti plasmid is described herein, but the invention is not so limited. The choice of particular bacterial vector involves no more than routine optimization of parameters by those of skill in the art. Other bacteria may be used including single T-DNA order constructs as well as others available to those of skill in the art through sources such as Genbank.

An "antisense oligonucleotide" is a molecule of at least 6 contiguous nucleotides, preferably complementary to DNA (antigene) or RNA (antisense), which interferes with the process of transcription or translation of endogenous proteins so that gene products are inhibited.

A "cloning vector" is a DNA molecule such as a plasmid, cosmid, or bacterial phage that has the capability of replicating autonomously in a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include those that provide resistance to antibiotics such as hygromycin, tetracycline, or ampicillin.

A "coding sequence" or "coding region" refers to a nucleic acid molecule having sequence information necessary to produce a gene product, when the sequence is expressed.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid that encodes a polypeptide of the present invention is implicit in each described polypeptide sequence and is within the scope of the present invention.

As to amino acid sequences, one of skill will recognize that individual substitutions, deletions, or additions to a nucleic acid, peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made.

Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

The term "co-suppression" is a method of inhibiting gene expression in organisms wherein a construct is introduced to an organism. The construct has one or more copies of sequence that is identical to or that shares nucleotide homology with a resident gene.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate *Macronucleus*, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both plant and fungi species, sequences can be modified to account for the specific codon preferences and GC content preferences as these preferences have been shown to differ, as described in the references cited herein.

The term "expression" refers to biosynthesis of a gene product. Structural gene expression involves transcription of the structural gene into mRNA and then translation of the mRNA into one or more polypeptides.

An "expression vector" is a DNA molecule comprising a gene that is expressed in a host cell. Typically, gene expression is placed under the control of certain regulatory elements including promoters, tissue specific regulatory elements, and enhancers. Such a gene is said to be "operably linked to" the regulatory elements.

As used herein, the term "fruit body" is intended to include tissue or cells from any of the sexual reproductive structure tissues from a fungus, other than vegetative mycelium and spores, including the cap, stem, gill, veil, volva, etc.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

As used herein the term "high stringency" shall mean conditions or hybridization equivalent to the following: hybridized for 12 hours at 42° C. in a buffer containing 50% formamide, 5×SSPE, 2% SDS, 10×Denhardt's solution, and 100 µg/ml salmon sperm DNA, and washing with 0.1×SSC, 0.1% SDS at 55° C. and exposed to Kodak X-Omat AR film for 4 days at −70° C.

By "host cell" is meant a cell that contains a vector and supports the replication and/or expression of the vector. Host cells may be prokaryotic cells such as *E. coli*, or eukaryotic cells such as fungi, insect, amphibian, or mammalian cells. Preferably, the host cells are fungal cells.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "polynucleotide construct" or "DNA construct" is sometimes used to refer to an expression construction. This also includes, however, antisense oligonucleotides or nucleotides designed for co-suppression of native host cell sequences or extrinsic sequences corresponding, for example, to those found in viruses.

The term "operably linked" means that the regulatory sequences necessary for expression of the coding sequence are placed in a nucleic acid molecule in the appropriate positions relative to the coding sequence so as to enable expression of the coding sequence. This same definition is sometimes applied to the arrangement of other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, phosphorylation, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation, which do not occur naturally. Circular, branched, and branched circular polypeptides may be synthesized by a non-translation natural process and by entirely synthetic methods, as well. Further, this invention contemplates the use of both the methionine-containing and the methionine-less amino terminal variants of the protein of the invention. With respect to a protein, the term "N-terminal region" shall include approximately 50 amino acids adjacent to the amino terminal end of a protein.

The terms "promoter", "promoter region", or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase. The term promoter includes the essential regulatory features of said sequence and may optionally include a long terminal repeat region prior to the translation start site.

A "recombinant host" may be any prokaryotic or eukaryotic cell that contains either a cloning vector or an expression vector. This term also includes those prokaryotic or eukaryotic cells that have been genetically engineered to contain the clone genes in the chromosome or genome of the host cell.

The term "reporter gene" refers to a gene that encodes a product that is easily detectable by standard methods, either directly or indirectly.

The term "selectable marker gene" refers to a gene encoding a product that, when expressed, confers a selectable phenotype such as antibiotic resistance on a transformed cell.

With respect to oligonucleotides or other single-stranded nucleic acid molecules, the term "specifically hybridizing" refers to the association between two single-stranded nucleic acid molecules of sufficiently complementary sequence to permit such hybridization under pre-determined conditions generally used in the art i.e., conditions of stringency (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "gene" is a DNA sequence that is transcribed into messenger RNA (mRNA), which is then translated into a sequence of amino acids characteristic of a specific polypeptide.

A "vector" is a replicon, such as plasmid, phage, cosmid, or virus to which another nucleic acid segment may be operably inserted so as to bring about the replication or expression of the segment.

DETAILED DESCRIPTION OF THE INVENTION

Figure 1:
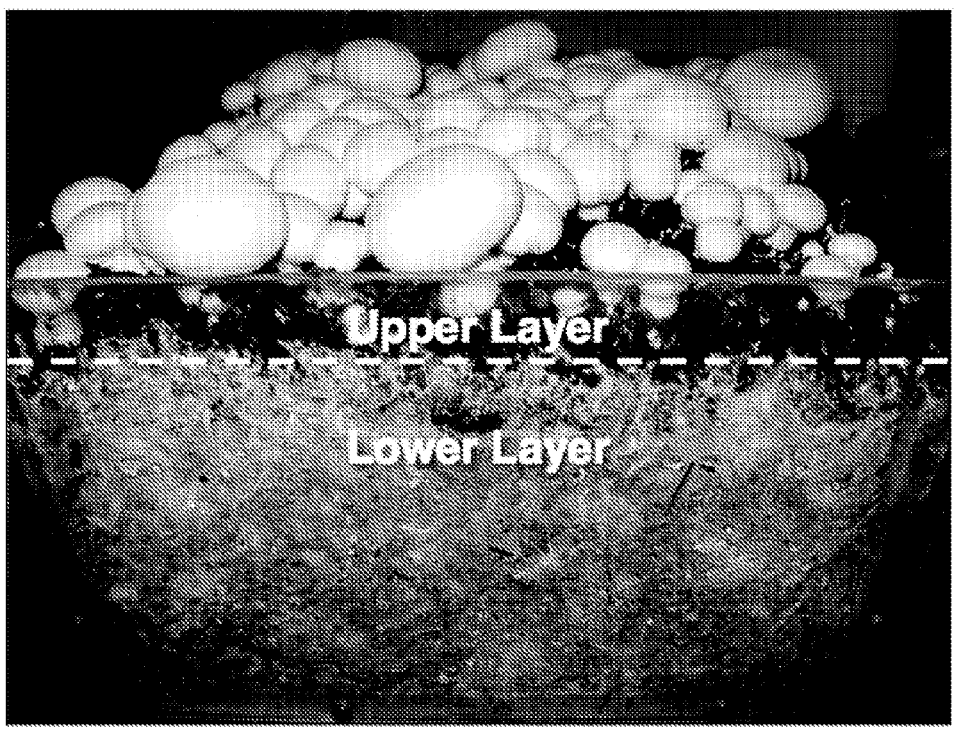
FIG. 1 is a photograph showing the cultivation scheme for the button mushroom, Agaricus bisporus. Shown is a cross-section of the bi-layered growth substrate consisting of a bed of compost (Lower Layer) and peat overlay (Upper Layer), which serve as the primary source of nutrients and water, respectively, for the developing fruiting body. The lower layer is seeded with an A. bisporus clonal inoculant and, during a 14-day period, the vegetative mycelium, shown imparting a white-color to the lower otherwise brown-colored compost layer, thoroughly colonizes the substrate. The upper layer of peat, which is also seeded with an A. bisporus inoculant, is then applied to the surface of the compost. The mycelia growing in the peat and compost physically fuse at the interface of the two layers (dashed line), forming a singular network throughout the growth medium. Harvest of the fruiting bodies begins at approximately 17 days after application of the peat layer.

The present technology is based upon the Applicants' discovery of a fundamentally new mechanism of protein synthesis/accumulation in fungi and a technique to independently control the genotype and phenotype of the fruiting body. The technology complements and extends methods known in the art for cultivating and creating transgenic mushrooms. The methods preferably use Agrobacterium-mediated genetic transformation of the edible mushroom (A. bisporus) by way of enabling expression of recombinant proteins in the high-biomass fruiting body (i.e. mushroom). Additionally, the new technology enables the transgenic modification of the fruiting body conferring an altered phenotype, but a wild-type genotype; the fruiting body itself being devoid of the cognate transgene.

The present invention allows for commercial applications in which filamentous fungi such as Agaricus species are employed as a production platform for high-value proteins (e.g. biopharmaceuticals, industrial enzymes, etc.). Additionally, this same technology could be used in the transgenic breeding of A. bisporus for enhanced agronomic traits, such as insect and virus resistance, heat tolerance, prolonged shelf life, etc., while maintaining the wild-type genotype of the fruiting body. Alternatively, the methodology could be used to achieve enhanced agronomic traits using combinations of non-transgenic mushroom lines.

Agaricus bisporus is grown in a composted mixture of plant and animal waste products. The compost substrate is seeded with the fungus using "spawn", which is cereal grain colonized by the vegetative mycelium of A. bisporus. After 14 days, the fungal mycelium has completely colonized the compost, at which time it is overlaid with a 5-cm layer of neutralized peat, referred to as the "casing". A second mycelial inoculant of A. bisporus, commonly referred to as the "CI", is mixed with the casing to promote the early and uniform formation of fruiting bodies (MacCanna and Flanagan 1972; Romaine and Schlagnhaufer 1992). At 17-19 days after casing, fruiting bodies first appear, and continue to develop in a rhythmic fashion at about weekly intervals.

Like all fungi, A. bisporus neither carries out photosynthesis to convert carbon dioxide into complex carbon compounds nor fixes atmospheric nitrogen (Alexopoulos et al. 1996). Consequently, carbon, nitrogen, and other nutrients required for its growth and development are derived exclusively from the organic matrix comprising the compost substrate. Mycelium emanating from the spawn secretes an array of hydrolytic enzymes that breakdown complex biopolymers in the compost. The low-molecular weight degradation products and simple molecules, such as sugars, are passively and actively transported into the fungal cells, which supports sustained mycelial growth through the compost substrate and, ultimately, the formation of the fruiting body.

While the lower compost substrate serves as the major food reservoir, the upper casing substrate functions as a water reservoir supporting the rapid cellular expansion of the developing fruiting body.

In the course of investigating the effect of various combinations of transgenic and wild-type (WT) mycelial inoculants in the upper and lower layers of the cultivation substrate on recombinant protein expression in the fruiting body of A. bisporus, two discoveries were made that provided the basis for the present invention. First, the genotype of the A. bisporus inoculant used in the upper layer strictly determined the genotype of the fruiting body. Hence, use of a transgenic inoculant in the upper layer gave rise to a transgenic fruiting body and a WT inoculant to a WT fruiting body. Here, it was critical to use a sufficiently high rate of inoculant in the upper layer to prevent the mycelium in the lower compost substrate from growing through the casing layer and participating in the formation of a chimeric fruiting body (WT/transgenic). And the second discovery, a recombinant protein expressed in the mycelium colonizing the lower substrate was translocated upward in to the developing fruiting body.

For the purpose of producing a fruiting body with a transgenic phenotype and WT genotype, the preferred method for carrying out the invention involves the use of a transgenic A. bisporus line as the inoculant for the lower layer and a WT line for the upper layer. Here, it is important that the transgenic line features a gene construct in which expression of the nucleotide sequence-of-interest, which encodes a protein and/or specific RNA sequence, is driven by a promoter that is highly active in the vegetative mycelium, such as the glyceraldehyde 3-phosphate dehydrogenase (GPD) promoter (Harmsen et al. 1992) and laccase2 (LCC2) promoter (Perry et al. 1993; Smith et al. 1998). In this manner, the protein and/or RNA transcript will be synthesized in the vegetative mycelium colonizing the lower-layer compost. In some applications of the invention, it is desirable for the protein and/or RNA transcript to be shuttled into the developing fruiting body, while in others it is preferred that the protein and/or RNA transcript remain confined to the mycelium in the compost. The difference being whether the presence of the expressed recombinant molecule must be directly present within the fruiting body tissues to affect a phenotypic change or if the phenotypic change in the fruiting body can be affected distally (i.e., as a consequence of expressing the recombinant protein and/or transcript in the mycelium colonizing the lower layer of compost). In either instance, since the WT inoculant used in the upper layer governs the genotype, the resultant fruiting body will have a WT genotype, as evidenced by the lack of the integrated transgene in the genome of its constituent cells. Examples illustrating this application of the invention are the incorporation of resistance to flies and LaFrance disease conferred by a transgenic line expressing a Bacillus thuringienesis toxin and LaFrance isometric virus RNA-derived hairpin transcript, respectively, as the inoculant for the lower layer, paired with a commercial WT line in the upper layer.

For the purpose of producing a WT fruiting body with an improved phenotype using exclusively WT lines, the preferred method for carrying out the invention involves pairing a WT line conferring a commercial desirable trait(s) in the fruiting body as the inoculant for the upper layer with a WT line having superior vegetative traits as the inoculant for the lower layer. The superior vegetative traits might include, but are not limited to, increased rate of compost colonization, thermal tolerance, resistance to pathogens and pests, such Trichoderma green mold and flies, and utilization of compost nutrients, and a capacity to utilize alternative compost ingredients. In effect, this technique allows for the combined use of two strains of A. bisporus to achieve desirable vegetative and reproductive traits that might otherwise might be either difficult or impossible to incorporate into a single strain.

For the purpose of achieving high-level protein production in the fruiting body, one preferred method of the invention involves pairing a lower-layer inoculant consisting of a transgenic line carrying the gene-of-interest driven by a promoter that is highly active in the vegetative mycelium, such as GPD or LCC2, with an upper-layer inoculant consisting of a transgenic line carrying the gene-of-interest driven by a promoter that is highly active in the fruiting body, as for example, hydrophobin A (HYPA) (De Groot et al. 1996). In a second preferred method, the lower and upper layers are inoculated with a single line of A. bisporus that is carrying the gene-of-interest driven by a promoter that is highly active in the vegetative mycelium and by a promoter that is highly active in the fruiting body. For both methods, high-level expression of the protein-of-interest in the fruiting body results from the combined long-distance translocation of the protein from the vegetative mycelium in the compost and in situ synthesis in the fruiting body. The expression of high-value biopharmaceuticals and industrial enzymes, which would be extracted and purified from the harvested fruiting body, are but a few examples illustrating this application of the invention.

The present invention can be carried out using conventional commercial practices for mushroom cultivation, including cultural and environmental regimes, substrate preparation and composition, inoculant matrices, and delayed-release supplements. However, depending on the particular characteristics of the A. bisporus lines used as the inoculants for the upper and lower layers, some modification of the inoculant rates and/or colonization times may be required. Generally, a conventional inoculant rate of 1 L of inoculant/0.6 m² of bed area, with a range of 1 L/0.5-0.75 m², and a 14-day incubation period, with a range of 7 to 21 days, can be used to achieve a thorough colonization of the lower layer of compost by A. bisporus mycelium. Similarly, a conventional inoculant rate of 1 L of inoculant/2.1 m² of bed area, with a range of 1 L/1.8 to 2.5 m², and a 17-day incubation period, with a range of 15 to 22 days, can be used to achieve a thorough colonization of the upper layer of peat by A. bisporus mycelium and formation of fruiting bodies. For any inoculant rate and incubation period regime, the overriding objective is to achieve thorough colonization of the upper and lower substrate layers by their respective inoculants, and to ensure that the upper layer is rapidly and thoroughly colonized by its mycelial inoculant, so as to prevent extensive intrusion by mycelium from the lower layer.

The preferred embodiment of the invention uses lines/strains/genotypes of A. bisporus for the lower-layer inoculant and upper-layer inoculant that are compatible for hyphal anastomosis, which involves the physical union of their vegetative mycelia. In this manner, the recombinant protein and/or other mobile molecule produced in the mycelium colonizing the lower layer can be freely translocated through the mycelium colonizing the upper layer and on into the developing fruiting body.

The invention thus contemplates the use of transgenic inoculant material for mushroom cultivation. This transgenic mushroom inoculant can be produced by any method known in the art and will preferably make use of Agrobacterium-mediated transformation.

Methods for the use of Agrobacterium-based transformation systems have been described for many different plant species. Agrobacterium tumefaciens is a gram-negative soil bacterium that causes crown gall tumors at wound sites of infected plants. During tumor induction, Agrobacterium transfers part of its tumor inducing (Ti) plasmid, the T-DNA, which is flanked by 24 bp imperfect direct repeats, to plant cells. The T-DNA then integrates into the plant DNA at random position. The process of T-DNA transfer depends on the induction of a set of virulence, (vir) genes, which are also located on the Ti plasmid. The vir genes are induced by compounds secreted from wounded plant cells such as acetosyringone (AS). In fungal transformation schemes, AS or other vir inducers must be added to induce vir gene activity. The ease of use, its efficiency of transformation, and the precision of T-DNA integration has led to widespread use of this organism for gene transfer into plants, and the development of transformation protocols for important crops including cereals such as rice and maize.

Generally, strains of bacteria, such as Agrobacterium tumefaciens, are used for genetic transformation that transfer part of its Ti plasmid to plants during tumorigenesis. Typically, the Agrobacterium used harbors modified versions of the naturally occurring Ti plasmid in which the oncogenes and the opaline metabolism genes have been removed such that the DNA is transferred to the host cells without the subsequent formation of tumors. These methods involve the insertion within the borders of the Ti plasmid the DNA to be inserted into the cellular genome linked to a selection marker gene to facilitate selection of transformed cells. Bacteria and recipient plant tissues are cultured together to allow transfer of foreign DNA into plant cells then transformed plants are regenerated on selection media. Any number of different organs and tissues can serve as targets for Agrobacterium-mediated transformation as described specifically for members of the Brassicaceae. These include thin cell layers (Charest, P. J., et al, 1988, Theor. Appl. Genet. 75:438-444), hypocotyls (DeBlock, M., et al, 1989, Plant Physiol. 91:694-701), leaf discs (Feldman, K. A., and Marks, M. D., 1986, Plant Sci. 47:63-69), stems (Fry J., et al, 1987, Plant Cell Repts. 6:321-325), cotyledons (Moloney M. M., et al, 1989, Plant Cell Repts. 8:238-242) and embryoids (Neuhaus, G., et al, 1987, Theor. Appl. Genet. 75:30-36). Agrobacterium-mediated transformation has been shown effective in many species of both monocotyledonous as well as dicotyledonous plants. Recently, Agrobacterium transformation has been confirmed in yeast. See, Bundock, et. al. "Trans-kingdom T-DNA transfer from Agrobacterium tumufaciens to Saccharomyces cerevisiae" The EMBO Journal vol. 14 no. 13 pp. 3206-3214, 1995. Interestingly, however, the transfer in yeast was shown to occur by a different mechanism than observed in plants. The authors conclude that the integration is predominately determined by host factors rather than the bacterium itself. This is important as depending on the particular host, integration may or may not occur depending on the host factors present. More recently, Agrobacterium-mediated transformation has been confirmed in A. bisporus, de Groot et al., but only with very low efficiency and a protracted procedure.

According to at least one embodiment of the invention, a polynucleotide construct to be introduced to a filamentous fungal cell by Agrobacterium, which acts as a vehicle for a transforming plasmid. Typically, a polynucleotide construct is inserted within the borders of a Ti plasmid containing functional vir genes, although the vir genes and polynucleotide need not be on the same plasmid.

Genetic transformation then occurs by simply incubating Agrobacterium with the fungal fruit body tissue cells. Subsequently, the bacterium is killed and the fruit body cells are allowed to regenerate under selective pressure to identify transformants.

Thus, the invention provides a transformed filamentous fungus inoculant obtainable by Agrobacterium-mediated transformation according to the invention not comprising any unwanted bacterial DNA sequence including a T-DNA border. Such transformed fungi can be used in a process for culturing a transformed fungus in order to produce a desired protein or specific nucleic acid sequence. Further, in accordance with the invention, short nucleic acid sequences, that may not encode a protein product, corresponding to some target gene (host or viral coded), might be expressed for the purpose of co-suppressive silencing. The invention also contemplates growing transgenic fungi for the mushrooms as a food, medicine, etc. and as a source of a desired protein (e.g., pharmaceutical production), as well as for the growth of vegetative mycelium as a source of a desired protein. Further, the protein may remain within the fungal cells requiring extraction, but the protein may also be secreted into the growth medium for recovery.

According to another embodiment of the invention a process is provided, in which the DNA fragment is randomly integrated in the fungal genome, as well as a transformed fungus obtainable by *Agrobacterium*-mediated transformation, which comprises one or more parts of T-DNA border sequences, and a process for culturing such transformed fungus in order to produce a desired protein or specific nucleic acid sequence.

The use of supervirulent *A. tumefaciens* strains is preferred, because they give a relatively high transformation frequency, such strains, the use thereof and vectors for making such strains are described in the literature; see Jin et al. (J. Bacteriology 169 (1987) 4417-4425 & Molecular Microbiology 7 (1993) 55-562), Raineri et al. (BIO/TECHNOLOGY 8 (January 1990) 33-38) and Ishida et al. (Nature Biotechnology 14 (1996) 745-750) for plant transformation, and Piers et al. (Proc. Nat'l. Acad. Sci. USA, 93 (1996) 1613-1618) for yeast transformation.

The transformation can be performed by a binary system where the vir genes act in trans or by co-integration with homologous recombination between a first plasmid and a wild-type Ti plasmid causing the oncogenes to be expelled from the plasmid in a similar way as known for plant transformation as discussed herein and known to those of skill in the art.

Production of a genetically modified fungal tissue either expressing or inhibiting expression of a gene combines the teachings of the present disclosure with a variety of techniques and expedients known in the art. In most instances, alternate expedients exist for each stage of the overall process. The choice of expedients depends on the variables such as the plasmid vector system chosen for the cloning and introduction of the recombinant DNA molecule, the fungal species to be modified, the particular structural gene, promoter elements, and upstream elements used. Persons skilled in the art are able to select and use appropriate alternatives to achieve functionality. Culture conditions for expressing desired structural genes and cultured cells are known in the art. Also as known in the art, a number of fungal species are transformable and regenerable such that the whole fungus, including all vegetative and reproductive tissues such as the mycelium, fruit bodies, and spores, containing and expressing desired genes under regulatory control of the promoter molecules according to the invention may be obtained. As is known to those of skill in the art, expression in transformed fungi may be tissue specific and/or specific to certain developmental stages. Truncated promoter selection and structural gene selection are other parameters that may be optimized to achieve desired fungal expression or inhibition as is known to those of skill in the art including single T-DNA border constructs and those and taught herein.

The following is a non-limiting general overview of molecular biology techniques that may be used in performing the methods of the invention.

The polynucleotide constructs of the present invention will share similar elements, which are well known in the art of molecular biology. For example, in each construct the DNA sequences of interest will preferably be operably linked (i.e., positioned to ensure the functioning of) to a promoter that allows the DNA to be transcribed (into an RNA transcript) and will comprise a vector that includes a replication system. In preferred embodiments, the DNA sequence of interest will be of exogenous origin in an effort to prevent co-suppression of the endogenous genes, unless co-suppression is the desired protocol.

Recombinant Heterologous Constructs

The present invention further provides fungal inoculation strains that incorporate recombinant heterologous constructs comprising a heterologous nucleic acid. A nucleic acid sequence coding for the desired polynucleotide of interest, for example a cDNA or a genomic sequence encoding a polypeptide long enough to code for an active protein, can be used to construct a recombinant expression cassette which can be introduced into the desired inoculation cell line. A recombinant expression cassette will typically comprise a polynucleotide operably linked to transcriptional initiation regulatory sequences that will direct the transcription of the polynucleotide in the intended host cell, such as tissues of a transformed fungi.

For example, expression vectors may include (1) a cloned fungal gene under the transcriptional control of 5' and 3' regulatory sequences and (2) a dominant selectable marker. Such expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal. In addition to expression cassettes, recombinant heterologous polynucleotide constructs can employ the use of inhibition sequences such as interfering RNA and the like. Recombinant constructs may be used either to up regulate expression of a heterologous gene, or as a inhibition construct for inhibition or down regulation of heterologous or endogenous genes, however all will share similar features as discussed herein.

Promoters

The constructs, promoters or control systems used in the methods of the invention may include a tissue specific promoter, an inducible promoter, or a constitutive promoter.

A large number of suitable promoter systems are available. For example, one constitutive promoter useful for the invention is the Cauliflower mosaic virus (CaMV) 35S. It has been shown to be highly active in many prokaryotic and eukaryotic species.

Promoters (and other regulatory elements) may be heterologous (i.e., not naturally operably linked to a DNA sequence from the same organism). Promoters useful for expression in fungi are known in the art and can be inducible, constitutive, tissue-specific, derived from eukaryotes, prokaryotes, or viruses, or have various combinations of these characteristics.

In choosing a promoter to use in the methods of the invention, it may be desirable to use a tissue-specific or developmentally regulated promoter. A tissue-specific or developmentally regulated promoter is a DNA sequence that regulates the expression of a DNA sequence selectively in the cells/tissues critical to a particular developmental period and/or function in the fungus. Any identifiable promoter may be used in the methods of the present invention that causes expression in fungi and there are many such promoters available. It may also be advantageous to use an inducible promoter to provide expression of the construct during controlled periods.

An inducible promoter may also be used in the instant invention. See Ward et al. *Plant Mol. Biol.* 22: 361-366 (1993). Exemplary inducible promoters include, but are not limited to, that from the ACE1 system which responds to copper (Mett et al. *PNAS* 90: 4567-4571 (1993)); In2 gene from maize which responds to benzenesulfonamide herbicide safeners (Hershey et al., *Mol. Gen. Genetics* 227: 229-237 (1991) and Gatz et al., *Mol. Gen. Genetics* 243: 32-38 (1994)) or Tet repressor from Tn10 (Gatz et al., *Mol. Gen. Genet.* 227: 229-237 (1991). A particularly preferred inducible promoter is a promoter that responds to an inducing agent to which fungi do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88: 0421 (1991).

These and other such promoters are known and accessible through sources such as Genbank. In a preferred embodiment, the promoter is homologous to the recipient host cell species. For example, in the *A. bisporus* transformation protocol, an *A. bisporus* glyceraldehyde 3-phosphate dehydrogenase (GPD) promoter is used in the polynucleotide construct. Two examples of fungi specific promoters include, but are not limited to, the GPD promoters from the fungi *A. nidulans*, (Mattern et. al. 1988, Fungal Genetics Newsletter 35:25), and *A. bisporus*, (Harmsen et. al. 1992 Current Genetics 22:447-454).

It may also be desirable to include some intron sequences in the promoter constructs since the inclusion of intron sequences in the coding region may result in enhanced expression and specificity.

Additionally, regions of one promoter may be joined to regions from a different promoter in order to obtain the desired promoter activity resulting in a chimeric promoter. Synthetic promoters that regulate gene expression may also be used.

The expression system may be further optimized by employing supplemental elements such as transcription terminators and/or enhancer elements.

Other Regulatory Elements

In addition to a promoter sequence, an expression cassette or polynucleotide construct should also contain a transcription termination region downstream of the structural gene to provide for efficient termination. The termination region or polyadenylation signal may be obtained from the same gene as the promoter sequence or may be obtained from different genes. Polyadenylation sequences include, but are not limited to the *Agrobacterium* octopine synthase signal (Gielen et al., *EMBO J.* (1984) 3:835-846) or the nopaline synthase signal (Depicker et al., *Mol. and Appl. Genet.* (1982) 1:561-573).

Transport of protein produced by transgenes to a subcellular compartment such as the vacuole, peroxisome, glyoxysome, cell wall or mitochondrion, or for secretion into the apoplast or growth medium, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately located. The presence of a signal sequence directs a polypeptide to either an intracellular organelle or subcellular compartment or for secretion to the apoplast or into the external environment. Many signal sequences are known in the art.

Marker Genes

Recombinant DNA molecules containing any of the DNA sequences and promoters described herein may additionally contain selection marker genes that encode a selection gene product conferring on a cell resistance to a chemical agent or physiological stress, or confers a distinguishable phenotypic characteristic to the cells such that cells transformed with the recombinant DNA molecule may be easily selected using a selective agent. One such selection marker gene is neomycin phosphotransferase (NPT II), which confers resistance to kanamycin and the antibiotic G-418. Cells transformed with this selection marker gene may be selected for by assaying for the presence in vitro of phosphorylation of kanamycin using techniques described in the literature or by testing for the presence of the mRNA coding for the NPT II gene by Northern blot analysis in RNA from the tissue of the transformed plant. Polymerase chain reaction (PCR) amplification is also used to identify the presence of a transgene or expression using reverse transcription-PCR amplification to monitor expression and PCR on genomic DNA. Other commonly used selection markers include the ampicillin resistance gene, the tetracycline resistance and the hygromycin (HPT) resistance gene. Transformed fungal cells thus selected can grow and develop into the vegetative mycelium, which will eventually yield the whole fungus, including the sexual reproductive structure (fruit body) and spores. It is to be understood that a selection marker gene may also be native to a fungus.

Proteins

With transgenic fungi according to the present invention, a recombinant protein can be produced in commercial quantities. Thus, techniques for the selection and propagation of transformed fungi, which are well understood in the art, yield a plurality of transgenic fungi that are harvested in a conventional manner, and a foreign protein then can be extracted from a tissue of interest or from total biomass, or secreted into the growth medium (liquid or solid state) and then recovered. Protein extraction from plant and fungal biomass can be accomplished by known methods which are discussed, for example, by Heney and Orr, *Anal. Biochem.* 114: 92-6 (1981), and in the references cited herein.

The recombinant protein of interest may be any protein appropriate for expression in prokaryotes, and can include industrial, therapeutic or agronomic proteins. Proteins that may produced by the instant invention include, but are not limited to, enzymes, regulatory proteins, receptors, peptides, e.g. peptide hormones, cytokines, membrane or transport proteins growth factors, antibodies and the, like. The protein of interest may be either homologous or heterologous to the host.

A protein of interest may be an enzyme which is selected from amylolytic enzymes, proteolytic enzymes, cellulolytic enzymes, oxidoreductase enzymes and plant wall degrading enzymes. Examples of these enzymes include amylases, proteases, xylanases, lipases, laccases, phenol oxidases, oxidases, cutinases, cellulases, hemicellulases, esterases, perioxidases, catalases, glucose oxidases, phytases, pectinases, glucosidases, isomerases, transferases, galactosidases and chitinases.

The proteins of interest may also be antigens as used for vaccination, vaccines, antigen-binding proteins, immune stimulatory proteins, allergens, full-length antibodies or antibody fragments or derivatives. Antibodies include, but are not limited to, immunoglobulins from any species from which it is desirable to produce large quantities. It is especially preferred that the antibodies are human antibodies. Immunoglobulins may be from any class, i.e., G, A, M, E or D. Antibody derivatives may be selected from the group of single chain antibodies, (sc $F_V$), Fab fragments, $F_V$ fragments, single domain antibodies ($V_H$ or $V_L$ fragment), domain antibodies like camelid single domain antibodies ($V_{HH}$, nanobodies) or other antibody formats as described for instance in Andersen and Reilly (2004) or Holliger and Hudson (2005). Hormones include, but are not limited to, follicle-stimulating hormone, luteinizing hormone, corticotropin-releasing factor, somatostatin, gonadotropin hormone, vasopressin, oxytocin, erythropoietin, insulin and the like. Growth factors are proteins that bind to receptors on the cell surface, with the primary result of activating cellular proliferation and/or differentiation. Growth factors include, but are not limited to, platelet-derived growth factor, epidermal growth factor, nerve growth factor, fibroblast growth factors, insulin-like growth factors, transforming growth factors and the like.

Cytokines are a unique family of growth factors. Secreted primarily from leukocytes, cytokines stimulate both the humoral and cellular immune responses, as well as the activation of phagocytic cells. Cytokines include, but are not limited to, colony stimulating factors, the interleukins (IL-1 α and β), IL-2 through IL-13) and the interferons. Human Interleukin-3 (IL-3) is a 15 kDa protein containing 133 amino acid residues. IL-3 is a species specific colony stimulating factor which stimulates colony formation of megakaryocytes, neutrophils, and macrophages from bone marrow cultures.

Other proteins of interest are mammalian proteins. Such proteins include, but are not limited to blood proteins (such as, serum albumin, Factor VII, Factor VIII (or modified Factor VIII), Factor IX, Factor X, tissue plasminogen factor, Protein C, von Willebrand factor, antithrombin III, and erythropoietin), colony stimulating factors (such as, granulocyte colony-stimulating factor (G-CSF), macrophage colony-stimulating factor (M-CSF), and granulocyte macrophage colony-stimulating factor (GM-CSF)), cytokines (such as, interleukins), integrins, addressins, selectins, homing receptors, surface membrane proteins (such as, surface membrane protein receptors), T cell receptor units, immunoglobulins, soluble major histocompatibility complex antigens, structural proteins (such as, collagen, fibroin, elastin, tubulin, actin, and myosin), growth factor receptors, growth factors, growth hormone, cell cycle proteins, vaccines, fibrinogen, thrombin, cytokines, hyaluronic acid and antibodies.

While for the most part, the product will be a peptidic product, genes may be introduced which may serve to modify non-peptidic products produced by the cells. These proteins, fragments thereof, usually of at least about 30 amino acids, fused combinations, mutants, and synthetic proteins, whether the proteins may be synthetic in whole or in part, so far as their sequence in relation to a natural protein, may be produced.

Likewise, by means of the present invention, agronomic genes can be expressed in transformed fungi. More particularly, fungi can be genetically engineered to express various phenotypes of agronomic interest. Exemplary genes implicated in this regard include, but are not limited to, those categorized below.

1. Genes that Confer Resistance to Pests or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (Arabidopsis RSP2 gene for resistance to *Pseudomonas syringae*).

(B) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt-endotoxin gene. Moreover, DNA molecules encoding-endotoxin genes can be purchased from American Type Culture Collection (Rockville, Md.), for example, under ATCC Accession Nos. 40098, 67136, 31995 and 31998.

(C) A lectin. See, for example, the disclosure by Van Damme et al., *Plant Molec. Biol.* 24: 25 (1994), who disclose the nucleotide sequences of several *Clivia miniata* mannose-binding lectin genes.

(D) A vitamin-binding protein, such as avidin. See PCT application US93/06487 the contents of which are hereby incorporated by. The application teaches the use of avidin and avidin homologues as larvicides against insect pests.

(E) An enzyme inhibitor, for example, a protease inhibitor or an amylase inhibitor. See, for example, Abe et al., *J. Biol. Chem.* 262: 16793 (1987) (nucleotide sequence of rice cysteine proteinase inhibitor), Huub et al., *Plant Molec. Biol.* 21: 985 (1993) (nucleotide sequence of cDNA encoding tobacco proteinase inhibitor I), and Sumitani et al., *Biosci. Biotech. Biochem.* 57: 1243 (1993) (nucleotide sequence of *Streptomyces nitrosporeus* alpha-amylase inhibitor).

(F) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(G) An insect-specific peptide or neuropeptide which, upon expression, disrupts the physiology of the affected pest. For example, see the disclosures of Regan, *J. Biol. Chem.* 269: 9 (1994) (expression cloning yields DNA coding for insect diuretic hormone receptor), and Pratt et al., *Biochem. Biophys. Res. Comm.* 163: 1243 (1989) (an allostatin is identified in *Diploptera puntata*). See also U.S. Pat. No. 5,266,317 to Tomalski et al., who disclose genes encoding insect-specific, paralytic neurotoxins.

2. Genes that Confer Resistance to a Herbicide, for Example:

(A) A herbicide that inhibits the growing point or meristem, such as an imidazalinone or a sulfonylurea. Exemplary genes in this category code for mutant ALS and AHAS enzyme as described, for example, by Lee et al., *EMBO J.* 7: 1241 (1988), and Miki et al., *Theor. Appl. Genet.* 80: 449 (1990), respectively.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSP that can confer glyphosate resistance. A DNA molecule encoding a mutant aroA gene can be obtained under ATCC Accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European Application No. 0 242 246 to Leemans et al. De Greef et al., *Bio/Technology* 7: 61 (1989), describe the production of transgenic plants that express chimeric bar genes coding for phosphinothricin acetyl transferase activity. Exemplary of genes conferring resistance to phenoxy proprionic acids and cycloshexones, such as sethoxydim and haloxyfop, are the Acc1-S1, Acc1-S2 and Acc1-S3 genes described by Marshall et al., *Theor. Appl. Genet.* 83: 435 (1992).

(C) A herbicide that inhibits photosynthesis, such as a triazine (psbA and gs+ genes) and a benzonitrile (nitrilase gene). Przibilla et al., *Plant Cell* 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

3. Genes that Confer or Contribute to a Value-Added Trait, Such as:

(A) Modified fatty acid metabolism, for example, by transforming a plant with an antisense gene of stearoyl-ACP desaturase to increase stearic acid content of the plant. See Knultzon et al., *Proc. Natl. Acad. Sci. USA* 89: 2624 (1992).

(B) Decreased phytate content
  (1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.
  (2) A gene could be introduced that reduces phytate content. In maize, this, for example, could be accomplished, by cloning and then reintroducing DNA associated with the single allele which is responsible for maize mutants characterized by low levels of phytic acid. See Raboy et al., *Maydica* 35: 383 (1990).

(C) Modified carbohydrate composition effected, for example, by transforming plants with a gene coding for an enzyme that alters the branching pattern of starch. See Shiroza et al., *J. Bacteriol.* 170: 810 (1988) (nucleotide sequence of *Streptococcus mutans* fructosyltransferase gene), Steinmetz et al., *Mol. Gen. Genet.* 200: 220 (1985) (nucleotide sequence of *Bacillus subtilis* levansucrase gene), Pen et al., *Bio/Technology* 10: 292 (1992) (production of transgenic plants that express *Bacillus licheniformis*-amylase), Elliot et al., *Plant Molec. Biol.* 21: 515 (1993) (nucleotide sequences of tomato invertase genes), Søgaard et al., *J. Biol. Chem.* 268: 22480 (1993) (site-directed mutagenesis of barley alpha-amylase gene), and Fisher et al., *Plant Physiol.* 102: 1045 (1993) (maize endosperm starch branching enzyme II).

Antisense or co-suppressive techniques may also be used according to the references disclosed herein.

In other embodiments, the activity of a polypeptide may be reduced or eliminated by disrupting the gene encoding the same. The invention encompasses mutagenized fungi that carry mutations in genes, where the mutations reduce expression the corresponding gene or inhibit the activity of the encoded of the encoded polypeptide.

Many methods may be used to reduce or eliminate the activity of a polypeptide. In addition, more than one method may be used to reduce the activity of a single polypeptide.

1. Polynucleotide-Based Methods:

In some embodiments of the present invention, an inoculation fungal strain is transformed with an expression cassette that is capable of expressing a polynucleotide that inhibits the expression of a polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one polypeptide is an expression cassette capable of producing an RNA molecule that inhibits the transcription and/or translation of at least one polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a polypeptide are given below.

i. Sense Suppression/Cosuppression

In some embodiments of the invention, inhibition of the expression of a polypeptide may be obtained by sense suppression or cosuppression. For cosuppression, an expression cassette is designed to express an RNA molecule corresponding to all or part of a messenger RNA encoding a polypeptide in the "sense" orientation. Over expression of the RNA molecule can result in reduced expression of the native gene. Accordingly, multiple fungal lines transformed with the cosuppression expression cassette are screened to identify those that show the greatest inhibition of polypeptide expression.

The polynucleotide used for cosuppression may correspond to all or part of the sequence encoding a polypeptide, all or part of the 5' and/or 3' untranslated region of a polypeptide transcript, or all or part of both the coding sequence and the untranslated regions of a transcript encoding a polypeptide. In some embodiments where the polynucleotide comprises all or part of the coding region for the polypeptide, the expression cassette is designed to eliminate the start codon of the polynucleotide so that no protein product will be translated.

Cosuppression may be used to inhibit the expression of genes to produce fungi having undetectable protein levels for the proteins encoded by these genes. See, for example, Broin, et al., (2002) *Plant Cell* 14:1417-1432. Cosuppression may also be used to inhibit the expression of multiple proteins in the same fungi. See, for example, U.S. Pat. No. 5,942,657. Methods for using cosuppression to inhibit the expression of endogenous genes in plants and fungi are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763; and U.S. Pat. Nos. 5,034,323, 5,283, 184, and 5,942,657; each of which is herein incorporated by reference. The efficiency of cosuppression may be increased by including a poly-dT region in the expression cassette at a position 3' to the sense sequence and 5' of the polyadenylation signal. See, U.S. Patent Publication No. 20020048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See U.S. Pat. Nos. 5,283,184 and 5,034,323; herein incorporated by reference.

ii. Antisense Suppression

In some embodiments of the invention, inhibition of the expression of the polypeptide may be obtained by antisense suppression. For antisense suppression, the expression cassette is designed to express an RNA molecule complementary to all or part of a messenger RNA encoding the polypeptide. Overexpression of the antisense RNA molecule can result in reduced expression of the native gene. Accordingly, multiple fungal lines transformed with the antisense suppression expression cassette are screened to identify those that show the greatest inhibition of polypeptide expression.

The polynucleotide for use in antisense suppression may correspond to all or part of the complement of the sequence encoding the polypeptide, all or part of the complement of the 5' and/or 3' untranslated region of the transcript, or all or part of the complement of both the coding sequence and the untranslated regions of a transcript encoding the polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same fungi. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550, or greater may be used. Methods for using antisense suppression to inhibit the expression of endogenous genes in fungi are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, U.S. Patent Publication No. 20020048814, herein incorporated by reference.

iii. Double-Stranded RNA Interference

In some embodiments of the invention, inhibition of the expression of a polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple fungi lines transformed with the dsRNA interference expression cassette or expression cassettes are then screened to identify fungi lines that show the greatest inhibition of polypeptide expression. Methods for using dsRNA interference to inhibit the expression of endogenous fungi genes are described in Waterhouse, et al., (1998) *Proc. Natl. Acad. Sci. USA* 95:13959-13964, Liu, et al., (2002) *Plant Physiol.* 129:1732-1743, and WO 99/49029, WO 99/53050, WO 99/61631, and WO 00/49035; each of which is herein incorporated by reference.

iv. Hairpin RNA Interference and Intron-Containing Hairpin RNA Interference

In some embodiments of the invention, inhibition of the expression of a polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Alternatively, the base-paired stem region may correspond to a portion of a promoter sequence controlling expression of the gene to be inhibited. Thus, the base-paired stem region of the molecule generally determines the specificity of the RNA interference. hpRNA molecules are highly efficient at inhibiting the expression of endogenous genes, and the RNA interference they induce is inherited by subsequent generations of fungi. See, for example, Chuang and Meyerowitz, (2000) *Proc. Natl. Acad. Sci. USA* 97:4985-4990; Stoutjesdijk, et al., (2002) *Plant Physiol.* 129:1723-1731; and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini et al., *BMC Biotechnology* 3:7, and U.S. Patent Publication No. 2003/0175965; each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407:319-320. In fact, Smith, et al., show 100% suppression of endogenous gene expression using ihpRNA-mediated interference. Methods for using ihpRNA interference to inhibit the expression of endogenous fungi genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295, and U.S. Patent Publication No. 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904; Mette, et al., (2000) *EMBO J.* 19:5194-5201; Matzke, et al., (2001) *Curr. Opin. Genet. Devel.* 11:221-227; Scheid, et al., (2002) *Proc. Natl. Acad. Sci., USA* 99:13659-13662; Aufsaftz, et al., (2002) *Proc. Nat'l. Acad. Sci.* 99(4):16499-16506; Sijen, et al., *Curr. Biol.* (2001) 11:436-440), herein incorporated by reference.

v. Amplicon-Mediated Interference

Amplicon expression cassettes comprise a fungal virus-derived sequence that contains all or part of the target gene, but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the polypeptide). Methods of using amplicons to inhibit the expression of endogenous fungi genes are described, for example, in Angell and Baulcombe, (1997) *EMBO J.* 16:3675-3684, Angell and Baulcombe, (1999) *Plant J.* 20:357-362, and U.S. Pat. No. 6,646,805, each of which is herein incorporated by reference.

vi. Ribozymes

In some embodiments, the polynucleotide expressed by the expression cassette of the invention is catalytic RNA or has ribozyme activity specific for the messenger RNA of the polypeptide. Thus, the polynucleotide causes the degradation of the endogenous messenger RNA, resulting in reduced expression of the polypeptide. This method is described, for example, in U.S. Pat. No. 4,987,071, herein incorporated by reference.

vii. Small Interfering RNA or Micro RNA

In some embodiments of the invention, inhibition of the expression of a polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of expression, the 22-nucleotide sequence is selected from a transcript sequence and contains 22 nucleotides of said sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of fungi.

In other embodiments, such fungi have stably incorporated into their genome a nucleic acid molecule comprising a nucleotide sequence of the invention operably linked to a promoter that drives expression in the cell.

Transformation

Traditional transformation techniques may be used in addition to *Agrobacterium* transfection. Other methods that have been employed for introducing recombinant molecules into plant cells involve mechanical means such as direct DNA uptake, liposomes, electroporation (Guerche, P. et al, 1987, *Plant Science* 52:111-116), and micro-injection (Neuhaus, G., et al, 1987, *Theor. Appl. Genet.* 75:30-36). The possibility of using microprojectiles and a gun or other device to force small metal particles coated with DNA into cells has also received considerable attention (Klein, T. M. et al., 1987, *Nature* 327:70-73).

It is often desirable to have the DNA sequence in homozygous state, which may require more than one transformation event to create a parental line; requiring transformation with a first and second recombinant DNA molecule both of which encode the same gene product. Another way to breed a transgenic homozygote is to individually transform two homokaryons (single-spores line carry a single nuclear type) of opposite mating type and cross them to create a fertile heterokaryotic line. It is further contemplated in some of the embodiments of the process of the invention that a fungal cell be transformed with a recombinant DNA molecule containing at least two DNA sequences or be transformed with more than one recombinant DNA molecule. The DNA sequences or recombinant DNA molecules in such embodiments may be physically linked, by being in the same vector, or physically separate on different vectors. A cell may be simultaneously transformed with more than one vector provided that each vector has a unique selection marker gene. Alternatively, a cell may be transformed with more than one vector sequentially allowing an intermediate regeneration step after transformation with the first vector. Further, it may be possible to perform a sexual cross between individual fungi or fungal lines containing different DNA sequences or recombinant DNA molecules preferably the DNA sequences or the recombinant molecules are linked or located on the same chromosome, and then selecting from the progeny of the cross, fungi containing both DNA sequences or recombinant DNA molecules.

Expression of recombinant DNA molecules containing the DNA sequences and promoters described herein in transformed fungi cells may be monitored using northern blot techniques and/or Southern blot techniques known to those of skill in the art.

The regenerated fungi are transferred to standard growing media (e.g., solid or liquid nutrient media, grain, vermiculite, compost, peat, wood, wood sawdust, straw, etc.) and grown or cultivated in a manner known to those practiced in the art.

After the polynucleotide is stably incorporated into regenerated transgenic fungi, it can be transferred to other fungi by sexual crossing. Any of a number of standard breeding techniques can be used, depending upon the species to be crossed.

It may be useful to generate a number of individual transformed fungi with any recombinant construct in order to recover fungi free from any positional effects. It may also be preferable to select fungi that contain more than one copy of the introduced recombinant DNA molecule such that high levels of expression of the recombinant molecule are obtained.

As indicated above, it may be desirable to produce fungal lines that are homozygous for a particular gene if possible in the particular species. In some species this is accomplished by the use monosporous cultures. By using these techniques, it is possible to produce a haploid line that carries the inserted gene and then to double the chromosome number either spontaneously or by the use of colchicine. This gives rise to a fungus that is homozygous for the inserted gene, which can be easily assayed for if the inserted gene carries with it a suitable selection marker gene for detection of fungi carrying that gene. Alternatively, fungi may be self-fertilized, leading to the production of a mixture of spores that consists of, in the simplest case, three types, homozygous (25%), heterozygous (50%) and null (25%) for the inserted gene. Although it is relatively easy to score null fungi from those that contain the gene, it is possible in practice to score the homozygous from heterozygous fungi by Southern blot analysis in which careful attention is paid to the loading of exactly equivalent amounts of DNA from the mixed population, and scoring heterozygotes by the intensity of the signal from a probe specific for the inserted gene. It is advisable to verify the results of the Southern blot analysis by allowing each independent transformant to self-fertilize, since additional evidence for homozygosity can be obtained by the simple fact that if the fungi was homozygous for the inserted gene, all of the subsequent fungal lines from the selfed individual will contain the gene, while if the fungus was heterozygous for the gene, the generation grown from the selfed seed will contain null fungal lines. Therefore, with simple selfing one can select homozygous fungal lines that can also be confirmed by Southern blot analysis.

Creation of homozygous parental lines makes possible the production of hybrid fungus and spores that will contain a modified protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The following examples are intended to further illustrate the invention and are not intended to limit the invention in any way. The examples and discussion herein may specifically reference *A. bisporus*, however the teachings herein are equally applicable to any other fungus, preferably filamentous fungi that bear fleshy fruit bodies including but not limited to *Agaricus* species blazei, bisporus, and bitorquis.

EXAMPLES

Methods

Commercial intermediate white hybrid strains of *A. bisporus* were used throughout this study. Wild-type cultures were maintained on malt extract agar (MEA; 20 g/l malt extract, 2.1 g/l MOPS pH 7.0, 15 g agar) and transgenic cultures on MEA containing 50 µg/ml hygromycin B.

Figure 2:
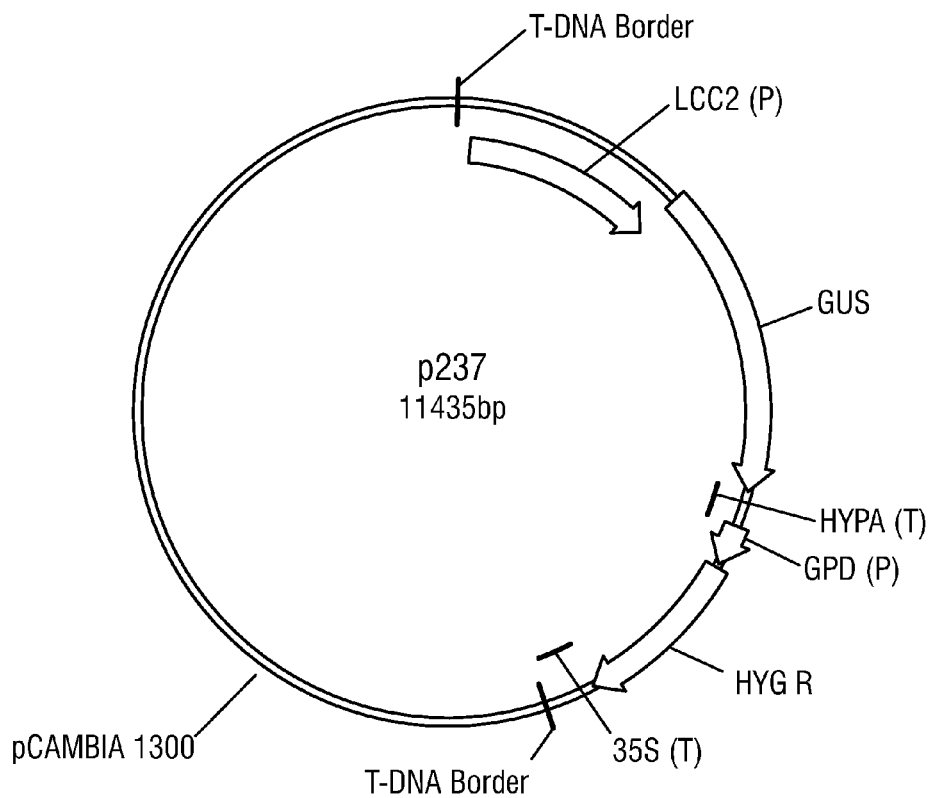
FIG. 2 is a map of the basic design of the Agrobacterium binary plasmid vector. Shown, as an example, is p237 containing the Agrobacterium T-DNA border sequences (T-DNA Border), Agaricus bisporus laccase 2 promoter [LCC2 (P)], β-glucuronidase gene (GUS), A. bisporus hydrophobin A terminator [HYPA (T)], A. bisporus glyceraldehyde 3-phosphate dehydrogenase promoter [GPD (P)], hygromycin phosphotransferase (HPT) gene for hygromycin selection (HYG$^R$), Cauliflower mosaic virus 35S terminator [35S (T)], and pCAMBIA 1300 backbone (pCAMBIA 1300).
Figure 3:
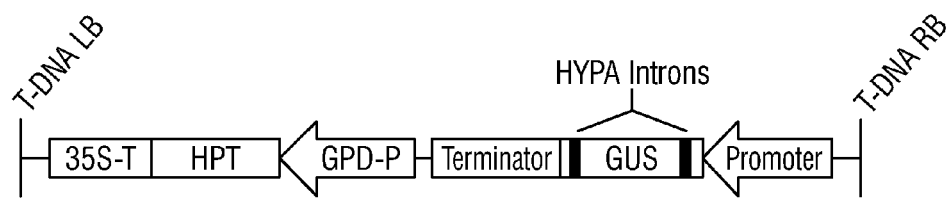
FIG. 3 is a linear map showing the structural organization of the expression cassette. The hygromycin phosphotransferase (HPT) gene, which conferred hygromycin resistance as a selectable marker, and GUS reporter gene (GUSPlus; CambiaLabs) (Broothaert et al. 2005) were situated between the left (T-DNA LB) and right (T-DNA RB) border sequences of the Agrobacterium T-DNA. The GUS gene was joined to either the native HYPA, LCC2, GPD, ACTN, LCTN or FBSD promoter (Promoter). GUS constructs contained the HYPA terminator sequence (Terminator), except for the FBSD construct, which incorporated the Arabidopsis polyubiquitin gene terminator (Callis et al. 1995). The positions of the HYPA introns within the GUS gene are shown. The HPT gene was linked to the native glyceraldehyde 3-phosphate dehydrogenase promoter (GPD-P) and Cauliflower mosaic virus 35S terminator (35S-T) (Chen et al. 2000). Promoter sequences of 552 bp, 1270 bp, and 264-bp were isolated from the native HYPA (De Groot et al. 1996), LCC2 (Perry et al. 1993; Smith et al. 1998), and GPD (Harmsen et al. 1992) genes, respectively, by PCR amplification of the DNA sequence directly upstream of the respective start codon. The LCTN, ACTN, and FBSD promoters were provided by Intrexon Corp., Germantown, Md. GUSPlus, which was modified by the addition of HYPA introns 2 and 3, was linked to a native promoter sequence at the Nco I restriction site. PCR-amplified sequences of 183 bp and 405 bp, downstream of the respective stop codon for the HYPA gene and Arabidopsis polyubiquitin gene, respectively, were used as terminators.

All experiments herein were carried out using transgenic lines of *A. bisporus* carrying a β-glucuronidase (GUS) reporter gene and hygromycin phosphotransferase (HPT) gene conferring resistance to the antibiotic, hygromycin B. FIGS. 2 and 3 depict a proprietary *Agrobacterium* binary plasmid vector (p237; Intrexon Corp.) and the general design of the expression cassette. This plasmid vector incorporates the basic features instructed by Chen et al. (2005 and 2009), including a pCAMBIA 1300 backbone with the HPT gene as a selection marker joined to the *A. bisporus* GPD promoter and Cauliflower mosaic virus 35S terminator, all of which are situated between the *Agrobacterium* T-DNA border sequences.

In the vector p237 example, the GUS gene is joined to the *A. bisporus* LCC2 promoter and HYPA terminator, which is placed between the T-DNA borders. Other GUS expression vectors employed in the present study had an identical design, but with the LCC2 promoter replaced by the either the native GPD or HYPA promoters and the proprietary (Intrexon Corp., Germantown, Md.) β-actin (ACTN), or lectin (LCTN) promoter (FIG. 3). For one vector, the GUS gene was joined to a proprietary native fruiting body-specific D (FBSD) promoter (Intrexon Corp.) and *Arabidopsis* polyubiquitin terminator (Callis et al. 1995).

*Agrobacterium*-mediated transformation using lamellae tissue of *A. bisporus* was performed as instructed by Chen et al. (2000) and Romaine and Schlagnhaufer (2006).

For the preparation of clonal mycelial inoculants, a 250-ml flask containing either 50 ml rye grain, 0.8 g calcium carbonate, 0.8 g calcium sulfate, and 60 ml Milli-Q water (lower layer inoculant) or 50 g of a proprietary matrix (Lambert Co., Coatesville, Pa. and Sylvan Inc., Kittanning, Pa.) and 75 ml Milli-Q water (upper layer inoculant) was autoclaved for 30 min. Each flask of inoculant was seeded with three mycelial agar blocks of *A. bisporus*, and kept at room temperature for 2-3 weeks with occasional shaking to redistribute the inoculum.

Mushroom cultivation was carried out using conventional practices and environmental parameters (Penn State 1982; Beyer 2003) as briefly summarized by Romaine and Schlagnhaufer (1992) with the following modifications: 15 g of lower-layer inoculant and 1.8 kg of compost were mixed and then packed in a 25-cm diameter plastic container, and 25 g of upper-layer inoculant and 1.5 L of the neutralized peat-based substrate were mixed and overlaid on the compost. Fruiting bodies were harvested, rinsed with water, diced, and stored as an aggregate sample by treatment at either −20° C. (PCR and GUS assay) or −78° C. (RT-PCR).

For the histological assay of GUS activity in fruiting bodies, longitudinal slices (2-3 mm thick) of freshly harvested fruiting bodies were incubated for 1.5-4 hr in 10 ml X-Gluc substrate (100 mM potassium phosphate pH 7.0, 25 mM ascorbic acid, 0.02% Triton X-100, 0.08% ethanol, 0.5 mg/ml 5-bromo-4-chloro-indoxyl-beta-D glucuronic acid (Gold Biotechnology, St. Louis, Mo.).

To analyze GUS enzyme activity in vegetative mycelium grown in compost, 1.75-cm holes were drilled into the sides of the 12-cm diameter plastic pots containing compost used for fruiting body production, and moistened 2.3-cm diameter Whatman 3MM filter paper discs were affixed with tape to cover the holes. After the 14-day compost *Agaricus* colonization phase, the discs were removed and placed in X-Gluc substrate for 2 hr.

To assess GUS activity in vegetative mycelium grown in axenic culture, a mycelial colony growing on MEA contained in a 6-cm diameter Petri plate was immersed in 5 ml X-Gluc substrate and incubated overnight.

For quantitative assay of GUS activity in fruiting bodies, frozen fruiting body tissue (3 g) was homogenized in 9 ml of extraction buffer (50 mM sodium phosphate pH 7.0, 10 mM EDTA, 10 mM mercaptoethanol, 0.1% Triton X-100, 0.1% sarkosyl) for 1 min with a PT 10-35 GT polytron (Kinematica, Inc., Lucerne, Switzerland). The extract was clarified at 11,000 g for 15 min and the protein concentration determined by the Bradford method (Bradford 1976).

GUS activity was quantified by a fluorometric assay with a 4-methylumbeliferyl B-D-glucuronide (MUG; Sigma, St. Louis, Mo.) substrate (O'Neill et al. 2008). The value was reported as the mean of the ratio of the molar rate of formation of 4-methyl-7-hexacoumarin (MU) to the total soluble protein.

To screen basidiospores for the co-transformed HPT gene conferring the hygromycin-resistance selection marker, a fruiting body approaching full maturity was soaked in a 10% commercial bleach solution (final concentration 0.6% NaClO) for 1 min, and then rinsed exhaustively with sterile Milli-Q water. Using a scalpel, the stem and veil tissue were excised to expose the lamellae, and the cap was suspended from a hooked wire over a sterilized 9-cm diameter filter paper disc within a sterilized glass chamber. After an overnight incubation, the discharged basidiospores were washed from the surface of the paper with sterile Milli-Q water. A 100-µl aliquot of a turbid basidiospore suspension (>100,000 basidiospores/ml as determined by hemocytometry) was spread onto each of a 10-cm diameter Petri plate of MEA and MEA containing 100 µg/ml hygromycin, and the plates were incubated at room temperature for 3-4 weeks.

To assay fruiting body tissue for hygromycin resistance, a 0.5-cm disc of internal cap tissue was transferred aseptically onto each of a 6-cm diameter Petri plate of MEA and MEA containing 50 µg/ml hygromycin. The plates were incubated at room temperature for 2-3 weeks.

DNA was extracted from frozen fruiting body tissue (100 mg) using the LETS procedure (Chen et al. 1999) with a FastPrep FP-120 system (Thermo Fisher Scientific, Waltham, Mass.). DNA was stored in TE buffer (10 mM Tris-HCl, 2 mM EDTA, pH 8.0) at −78° C.

RNA was extracted from frozen fruiting body tissue (100 mg) using the RNAqueous Kit (Applied Biosystems, Foster City, Calif.) and FastPrep system. RNA was treated with 2 U DNAse in Tris-HCl pH 7.5, 2.5 mM $MgCl_2$, 0.5 mM $CaCl_2$ at 37° C. for 1 hr, followed by standard phenol extraction and ethanol precipitation. RNA was stored in TE buffer at −78° C.

PCR amplification was carried out in a final volume of 25 μl containing 0.75 U Taq DNA polymerase with Standard Taq Buffer (New England Biolabs, Ipswich, Mass.), 200 μM dNTPs, 0.2 μM each primer and 10-50 ng DNA template. Primer set I: Fwd 5'CGTGACAAGAACCATCCAAGCG3' (SEQ ID NO:1) and Rev 5'GGGTAGCCATCACAAACAG CAC3' (SEQ ID NO:2)were used to amplify a 163-bp sequence in the GUS gene. Alternatively, primer set II was employed: Fwd 5'CGAACTAGTCTGTACCCGATCAA-CACC3' (SEQ ID NO:3) and Rev 5'TCCGCACGC-CGAACGGCTCTTC3' (SEQ ID NO:4) which defined a 835-bp sequence in the GUS gene. As a DNA template control, a separate reaction was run using either primer set: Fwd 5'CGACGGGTGTGAACGCAAAGG3' (SEQ ID NO:5) and Rev 5'CAATCAG TCGATCAACGTTCGC3' (SEQ ID NO:6) which defined a 403-bp sequence in the native polyphenol oxidase 1 (PPO) gene (Wichers et al. 2003) or primer set: Fwd 5'GGAAGTTTAGATAGGGGACC3' (SEQ ID NO:7) and Rev 5'GTGGCTGTCTGAAAAGATAC3' (SEQ ID NO:8), which defined a 500-bp sequence in the native aldolase dehydrogenase (ALD) gene (Genbank sequence accession no. Y17825). Thermocycling parameters were: 94° C. for 5 min; 35 cycles of 94° C. for 1 min, 58° C. for 1 min and 72° C. for 1 min.

RT-PCR was performed (25 μl final volume) with a Mas-terAmp RT-PCR Kit (Epicentre Biotechnologies, Madison, Wis.) using 30-100 ng RNA template and the PCR primer sets for the GUS (primer set II) and PPO genes in separate reactions. Thermocycling parameters were: 60° C. for 20 min; 94° C. for 2 min; 40 cycles of 94° C. for 1 min and 60° C. for 1 min; 72° C. for 7 min.

Real-time qPCR was carried out employing the standard protocol at the Huck Institute Genomics Core Facility, The Pennsylvania State University, University Park, Pa. GUS primers were: Fwd 5'CGACGGACTGACCATCGAT3' (SEQ ID NO:9), and Rev 5'GAACTTGCCGTCGTTGACTTC3' (SEQ ID NO:10), with a 5'FAM-CCGTTCGGCGTGCG-GACC3' (SEQ ID NO:11), BHQ probe sequence. ACTN primers were: Fwd 5'ATGCTCCTCGTGCCGTCTT3' (SEQ ID NO:12), and Rev 5'TGCCCCATACCAACCATCA3' (SEQ ID NO:13), with a 5'FAM-CCTTCCATCGTCG-GTCGTCCTCG3' (SEQ ID NO:14), BHQ probe sequence. Amplification parameters were: 95° C. for 10 min; 40 cycles of 95° C. for 15 sec and 60° C. for 1 min, using a 7300 Real-time Sequence Detection System (Applied Biosystems). Ct values of the GUS gene and the reference ACTN gene were used with the delta delta Ct method to determine relative levels.

Example 1

Commercial cultivation of *A. bisporus* is carried out on a bi-layered substrate consisting of an upper peat layer and a lower compost layer (FIG. 1), each of which is seeded with a mycelial inoculant. As considerably less inoculant is required to colonize the thin upper layer, a dual-inoculant strategy where a standard WT inoculant is used to seed the lower layer could reduce the transgenic inoculant requirement for biomass production by approximately 70% and shorten the recombinant protein manufacturing time by more than two weeks. Thus, the practice was evaluated of affecting recombinant protein production through the application of a transgenic GUS-expressing *A. bisporus* mycelial inoculant (denoted XGS, where X refers to the promoter used to drive expression of the GUS transgene) to the upper layer and a WT inoculant to the lower layer. Using an inoculant notation system herein of "upper layer inoculant/lower layer inoculant", this treatment is designated "XGS/WT".

Histological GUS Assay of Vegetative Mycelium.

To analyze GUS enzyme activity in vegetative mycelium grown in compost, 1.75-cm holes were drilled into the sides of the 12-cm diameter plastic pots containing compost used for fruiting body production, and moistened 2.3-cm diameter Whatman 3MM filter paper discs were affixed with tape to cover the holes. After the 14-d compost *Agaricus* colonization phase, the discs were removed and placed in X-Gluc substrate for 2 h.

To assess GUS activity in vegetative mycelium grown in axenic culture, a mycelial colony growing on MEA contained in a 6-cm diameter Petri plate was immersed in 5 ml X-Gluc substrate and incubated overnight.

Fruiting Body cDNA Library.

Figure 4:
FIG. 4 is a chart showing the GUS genotype and phenotype of the first-harvest fruiting bodies grown using wild-type and transgenic inoculants. Indicated is the upper layer inoculant/lower layer inoculant for the bi-layered cultivation substrate. Wild-type (WT) line; GUS line carrying the HYPA promoter (HGS), GPD promoter (GGS), and LCC2 promoter (LGS). Shown are the results of histological and quantitative assays for GUS activity. For the latter, activity is expressed as nmol MUG hydrolyzed/min/100 μg of total soluble protein, where n=2. Percentage in parentheses expresses the mean value for the dual inoculant treatment relative to its respective single transgenic inoculant treatment at 100%. Also shown are the results of a qPCR analysis for the GUS gene. Value represents the mean normalized to the endogenous ACTN gene, where n=3; (s.d.).

Total RNA was extracted from freshly harvested fruiting bodies (maturity stage 3-4) using Tri-Reagent solution (Ambion, Inc.), and poly(A)+ RNA was isolated using oligo-(dT) 15 cellulose (Promega Corp.)." First-strand cDNAs were synthesized by reverse transcription using an oligo-dT primer with a Xho I restriction endonuclease site, which was followed by second-strand synthesis using DNA polymerase I in the presence of RNase H. Double-stranded cDNAs were ligated at their 5'-ends to an EcoRI adaptor and cloned in pBluescriptII XR vector (Agilent Technologies Corp.). A total of 4,608 bacterial colonies were spotted on Hybond-N membrane (GE Healthcare) and probed with synthesized gene-specific DNA oligos (60 nt) (Integrated DNA Technologies) that were labeled using an ECL Direct DNA/RNA Labeling/Detection Kit (GE Healthcare) The findings of exploratory studies suggested the dual-inoculant approach can provide a substantial level of recombinant protein production (GUS enzyme activity), but its efficacy depended on the promoter used to drive expression of the GUS gene. For example, when a transgenic *A. bisporus* line (HGS) carrying the GUS gene controlled by the HYPA promoter was used as the inoculant for the upper layer along with a WT line-inoculated lower layer (HGS/WT), fruiting bodies expressed 63% of the GUS activity observed for the treatment HGS/HGS where both layers were seeded with the transgenic inoculant (FIG. 4). In sharp contrast, employing a transgenic line that carried the GUS gene driven by either the GPD promoter (line GGS) or LCC2 promoter (line LGS) as the upper-layer inoculant (XGS/WT) resulted in a 100% loss in GUS activity.

Figure 5:
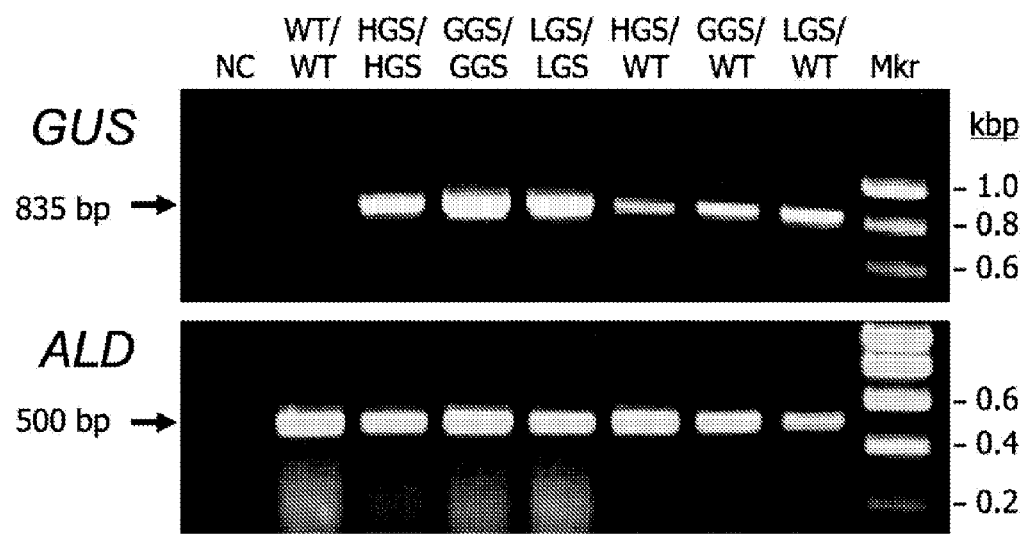
FIG. 5 shows PCR analysis of the GUS gene in fruiting bodies grown using wild-type and transgenic inoculants. Indicated is the upper layer inoculant/lower layer inoculant for the bi-layered cultivation substrate. Wild-type (WT) line; GUS line carrying the HYPA promoter (HGS), GPD promoter (GGS), and LCC2 promoter (LGS); No template PCR control (NC); DNA markers (Mkr) with sizes in kbp are indicated. Shown are the expected 835-bp and 500-bp amplicons for the GUS gene (GUS) and endogenous aldolase dehydrogenase gene (ALD), respectively.

Irrespective of the inoculant treatment, results of qPCR analysis revealed the presence of the GUS gene in the fruiting body (FIG. 4). However, fruiting bodies produced from a dual inoculant combination (XGS/WT) showed an approximate 25-50% reduction in the GUS gene dose compared to that in fruiting bodies grown from a single transgenic inoculant (XGS/XGS). The presence of the GUS gene in the fruiting bodies, as determined by qPCR analysis, was corroborated by the findings of non-quantitative PCR analysis (FIG. 5).

The results of Example 1 were consistent with the formation of a chimeric fruiting body (GUS/WT) related to the transgenic and WT dual-inoculant condition. It is likely that the WT line in the lower layer had a relatively higher growth rate compared to the transgenic lines, which resulted in intrusion and invasion of the upper layer. Nonetheless, the up to 50% reduction in level of the GUS gene owing to the use of a dual inoculant could not explain the 100% loss of GUS activity associated with lines LGS and GGS.

Example 2

Figure 6:
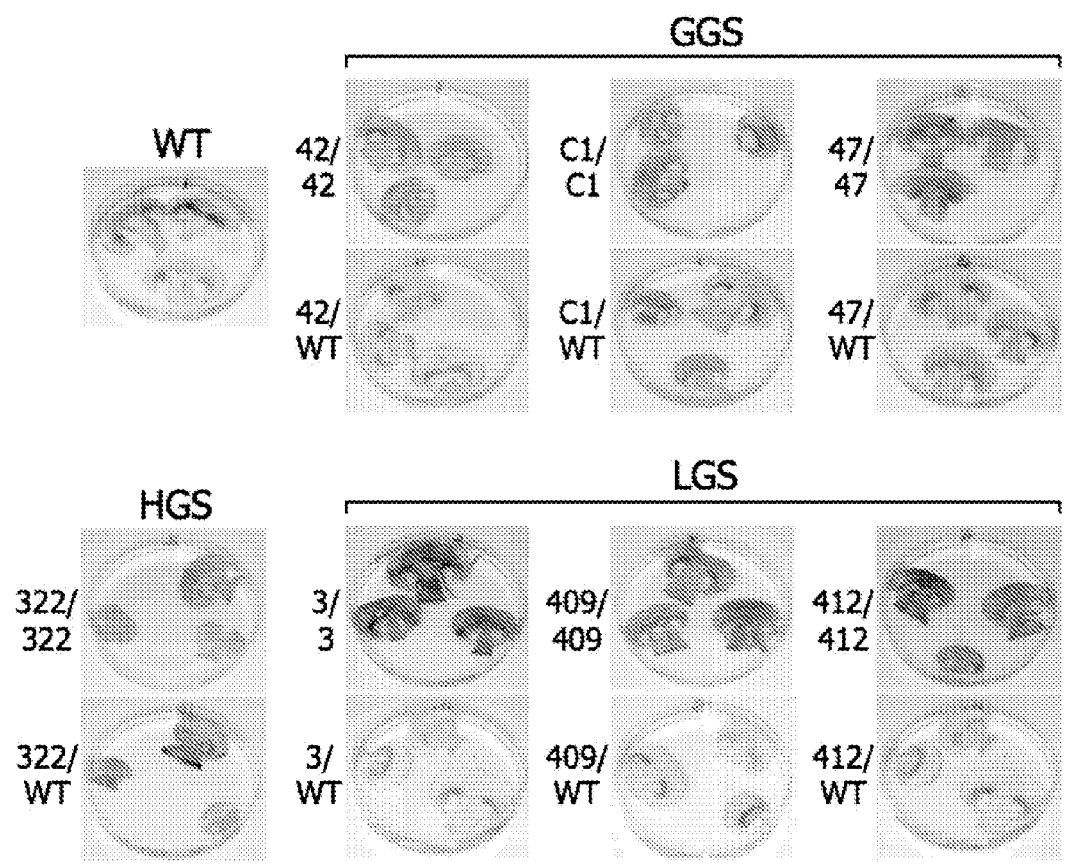
FIG. 6 shows the GUS activity in fruiting bodies grown using wild-type and transgenic inoculants from Example 2. Indicated is the upper layer inoculant/lower layer inoculant for the bi-layered cultivation substrate. Wild-type (WT) line; GUS line carrying the GPD promoter (GGS); GUS line carrying the HYPA promoter (HGS); GUS line carrying the LCC2 promoter (LGS); 42, CI, 47, 322, 3, 409, and 412 denote different transgenic lines. A near complete loss of GUS activity was observed in the fruiting body when either a GGS or LGS line was used in the upper layer in combination with a WT line in the lower layer (XGS/WT) relative to the level obtained with a completely transgenic inoculant (XGS/XGS). In contrast, line HGS yielded relatively high-level GUS activity when employed as the inoculant for the upper layer over a WT-inoculated lower layer.

This example was essentially identical to Example 1, except three independent transgenic lines for each of GGS and LGS were evaluated. As observed in Example 1, fruiting bodies with appreciable GUS activity could be grown using a substrate in which a GUS line was used in the upper layer in combination with a WT line in the lower layer. However, the level of enzyme activity observed varied with the promoter driving the GUS gene. (FIG. 6 and Table 1).

TABLE 1

Example 2 - Quantitative GUS activity assay of fruiting bodies grown using wild-type and transgenic inoculants.

| Agaricus bisporus Line[1] | GUS Activity[2] | | % Reduction |
|---|---|---|---|
| | Single Inoculant[3] | Dual Inoculant[4] | |
| WT | 0.07[5] (0.03-0.10) | — | — |
| HGS | 1.04 (1.02-1.05) | 0.83 (0.78-0.88) | 20 |
| GGS-42 | 1.44 (1.43-1.44) | 0.00 (0.00-0.00) | 100 |
| GGS-C1 | 3.25 (3.16-3.35) | 0.17 (0.17-0.18) | 95 |
| GGS-47 | 2.26 (2.17-2.34) | 0.00 (0.00-0.00) | 100 |
| LGS-3 | 19.14 (18.2-20.1) | 0.26 (0.26-0.26) | 99 |
| LGS-409 | 7.12 (6.59-7.66) | 0.23 (0.23-0.24) | 97 |
| LGS-412 | 5.30 (4.87-5.80) | 0.13 (0.12-0.15) | 98 |

[1]WFootnotes not visible in Macild-type (WT) line; GUS line carrying the HYPA promoter (HGS), GPDGPD promoter (GGS), and LCC2 promoter (LGS); 42, C1, 47, 3, 409, and 412 denote different transgenic lines.
[2]nmol MUG hydrolyzed/min/100 μg of total soluble protein.
[3]Both upper and lower layers were inoculated with the indicated line.
[4]Upper layer was inoculated with the indicated line and lower layer with a WT line.
[5]Value represents the mean, where n = 2; (value range).

The highest level of GUS activity of 80% (i.e. 20% reduction) was obtained with line HGS carrying the HYPA promoter line relative to the enzyme activity level observed with the completely transgenic inoculant control (HGS/HGS). Once again, and in sharp contrast, GUS activity was reduced by 95-100% when any one of the six GGS and LGS lines, carrying the GPD and LCC2 promoter, respectively, was used in the upper layer atop a WT-inoculated lower layer.

Table 2 summarizes the outcome of qPCR analysis of the GUS gene in fruiting bodies grown from the various single- and dual-inoculant treatments. With but one possible exception (line LGS-409), fruiting bodies grown using dual-inoculant combinations comprising a transgenic line and WT line showed no significant reduction in the level of the GUS gene relative to the gene level found in fruiting bodies grown from their respective completely transgenic inoculant control. This finding indicated that the fruiting bodies produced by the dual-inoculant condition were not chimeric in nature. As observed in Example 1, the dramatic loss of GUS activity in fruiting bodies grown from a combination of the WT line and either line GGS or line LGS could not be explained by a corresponding diminution in the level of the GUS gene.

TABLE 2

Example 2 - qPCR analysis of the GUS gene in fruiting bodies grown using wild-type and transgenic inoculants.

| Upper Layer Inoculant/ Lower Layer Inoculant[1] | Relative GUS Gene Value[2] |
|---|---|
| HGS/HGS | 571 (±124) |
| HGS/WT | 642 (±129) |
| GGS-42/GGS-42 | 1,611 (±285) |
| GGS-42/WT | 1,850 (±315) |
| GGS-C1/GGS-C1 | 1,692 (±162) |
| GGS-C1/WT | 2,343 (±731) |
| GGS-47/GGS-47 | 2,096 (±167) |
| GGS-47/WT | 2,065 (±114) |
| LGS-3/LGS-3 | 2,734 (±712) |
| LGS-3/WT | 2,711 (±330) |
| LGS-409/LGS-409 | 753 (±101) |
| LGS-409/WT | 680 (±7) |
| LGS-412/LGS-412 | 517 (±98) |
| LGS-412/WT | 659 (±34) |

[1]Wild-type (WT) line; GUS line carrying the HYPA promoter (HGS), GPDGPD promoter (GGS), and LCC2 promoter (LGS); 42, C1, 47, 3, 409, and 412 denote different transgenic lines.
[2]Value represents the mean normalized to the endogenous ACTN gene, where n = 3; (s.d.).

Example 3

Figure 7:
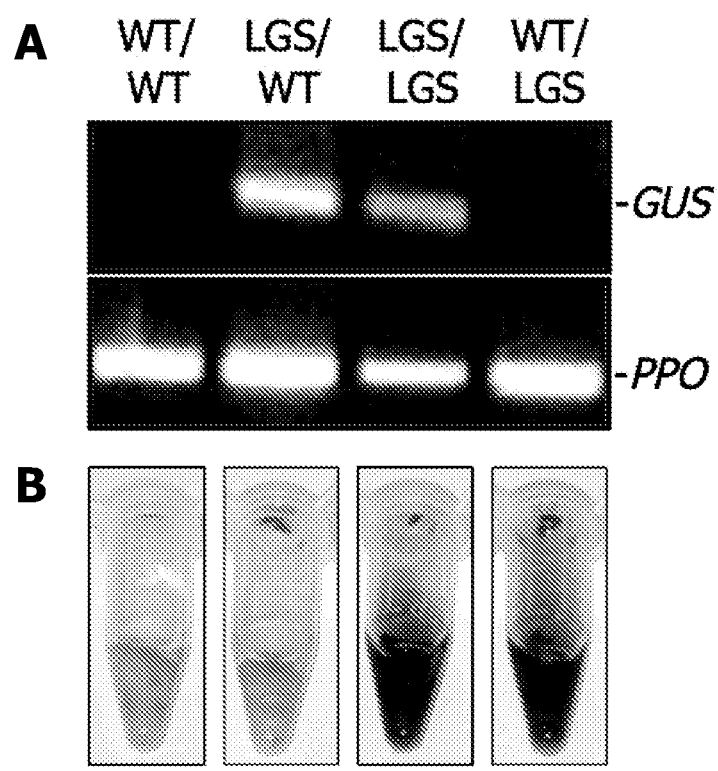
FIG. 7 shows the GUS genotype and phenotype of fruiting bodies grown using wild-type and transgenic inoculants from Example 3. Indicated is the upper layer inoculant/lower layer inoculant for the bi-layered cultivation substrate. Wild-type (WT) line; GUS line carrying the LCC2 promoter (LGS). (A) PCR analysis of the fruiting bodies for the GUS gene showing the predicted 163-bp amplicon (GUS) and the 500-bp amplicon for the endogenous polyphenol oxidase (PPO) gene. (B) Histological assay for GUS activity.

In this trial, a WT and an LGS line carrying the LCC2 promoter were used in all possible combinations to inoculate the upper and lower layers of the cultivation substrate. If the WT line was used to inoculate both layers, then the fruiting bodies showed both a WT genotype and phenotype, being PCR-negative for the GUS gene and lacking GUS enzyme activity (FIG. 7). Similarly, use of the LGS line as an inoculant for both layers resulted in a fruiting body with both a GUS genotype and phenotype, as evidenced by the PCR-detected GUS gene and GUS enzyme activity. As observed in Examples 1 and 2, inoculating and the upper layer with the LGS line and the lower layer with the WT line (LGS/WT) yielded fruiting bodies showing a GUS genotype (PCR-positive), but WT phenotype; expressing from none to a trace-level of GUS enzyme activity. Interestingly, when the inoculants were inverted: the WT line in the upper layer and GUS line in the lower layer (WT/LGS), then the traits of the fruiting body became reversed, exhibiting a WT genotype (PCR-negative for the GUS gene) and GUS phenotype (expressing high-level GUS activity).

Results of this study confirmed and extended those of Examples 1 and 2. For all inoculant treatments, the genotype of the fruiting body was strictly determined by the GUS genotype of the *A. bisporus* line introduced to the casing layer. We also established that the genotype was not predictive of the GUS phenotype of the fruiting body.

Example 4

Figure 8:
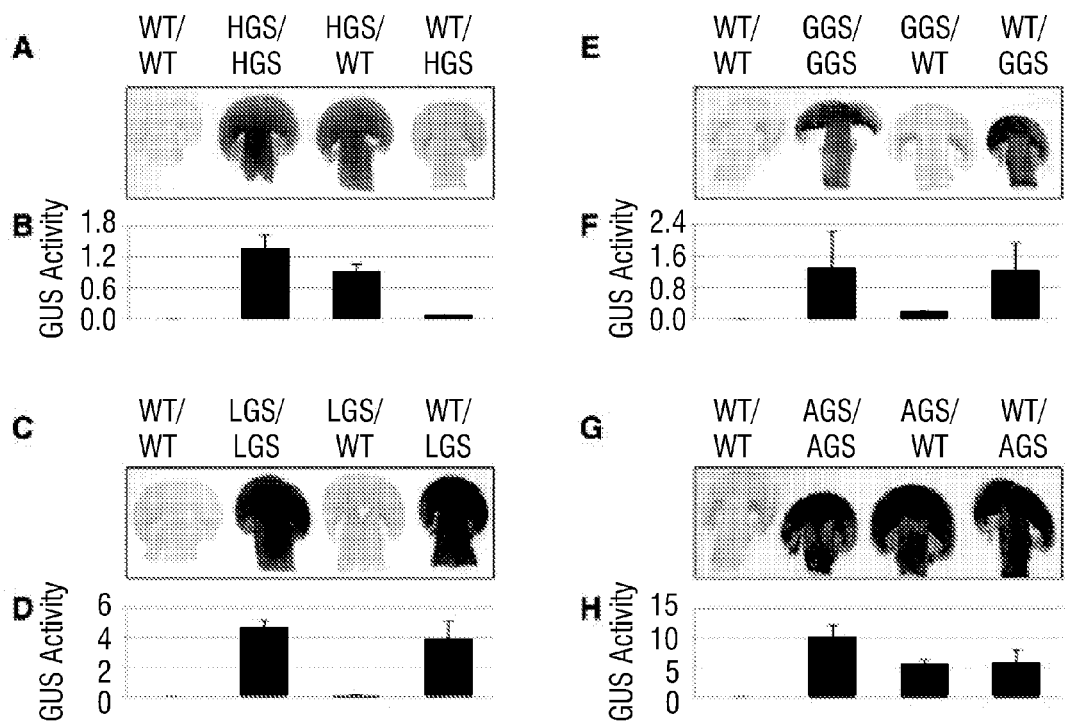
FIG. 8 shows the GUS activity assay of fruiting bodies grown using wild-type and transgenic inoculants from Example 4. Indicated is the upper layer inoculant/lower layer inoculant for the bi-layered cultivation substrate. Wild-type (WT) line; GUS lines carrying the HYPA promoter (HGS), LCC2 promoter (LGS), GPD promoter (GGS), and ACTN promoter (AGS). Shown are the results of histological and quantitative assays of GUS activity in fruiting bodies for lines (A,B) HGS, (C,D) LGS, (E,F) GGS, and (G, H) AGS. For the quantitative assay, GUS activity is expressed as nmol MUG hydrolyzed/min/100 µg of total soluble protein, and represents the mean value of two independent experiments.

A full factorial design experiment was conducted in which *A. bisporus* lines expressing GUS driven by four different promoters were each paired with a WT line as inoculants for the two layers. These studies included lines HGS, LGS, and GGS as well as AGS, which has the GUS gene driven by the β-actin (ACTN) promoter. Consistent with the observations from the previous examples where the GUS lines were employed in the upper layer, fruiting bodies from HGS/WT yielded approximately 70% of the maximal GUS activity obtained with HGS/HGS (FIG. 8 A,B), whereas fruiting bodies from LGS/WT (FIG. 8 C,D), and GGS/WT (FIG. 8 E,F), showed a >95% reduction in activity relative to the activity for LGS/LGS and GGS/GGS, respectively. In contrast, line AGS showed an approximately 50% yield of GUS activity in fruiting bodies from AGS/WT compared to the activity observed for AGS/AGS (FIG. 8 G,H).

Each dual-inoculant treatment was also examined in the inverse conformation, with the WT inoculant in the upper layer and GUS inoculant in the lower layer. Fruiting bodies from the WT/HGS now showed a >95% reduction in GUS activity observed from the HGS/HGS fruiting bodies (FIG. 8 A,B). Unexpectedly, WT/LGS (FIG. 8 C,D) and WT/GGS (FIG. 8 E,F) fruiting bodies showed 80% of the GUS activity observed from LGS/LGS and GGS/GGS fruiting bodies, respectively. Line AGS proved largely unaffected by the spatial transposition of the inoculants, as fruiting bodies from AGS/WT and WT/AGS showed similar levels of GUS activity (FIG. 8 G,H).

Figure 9:
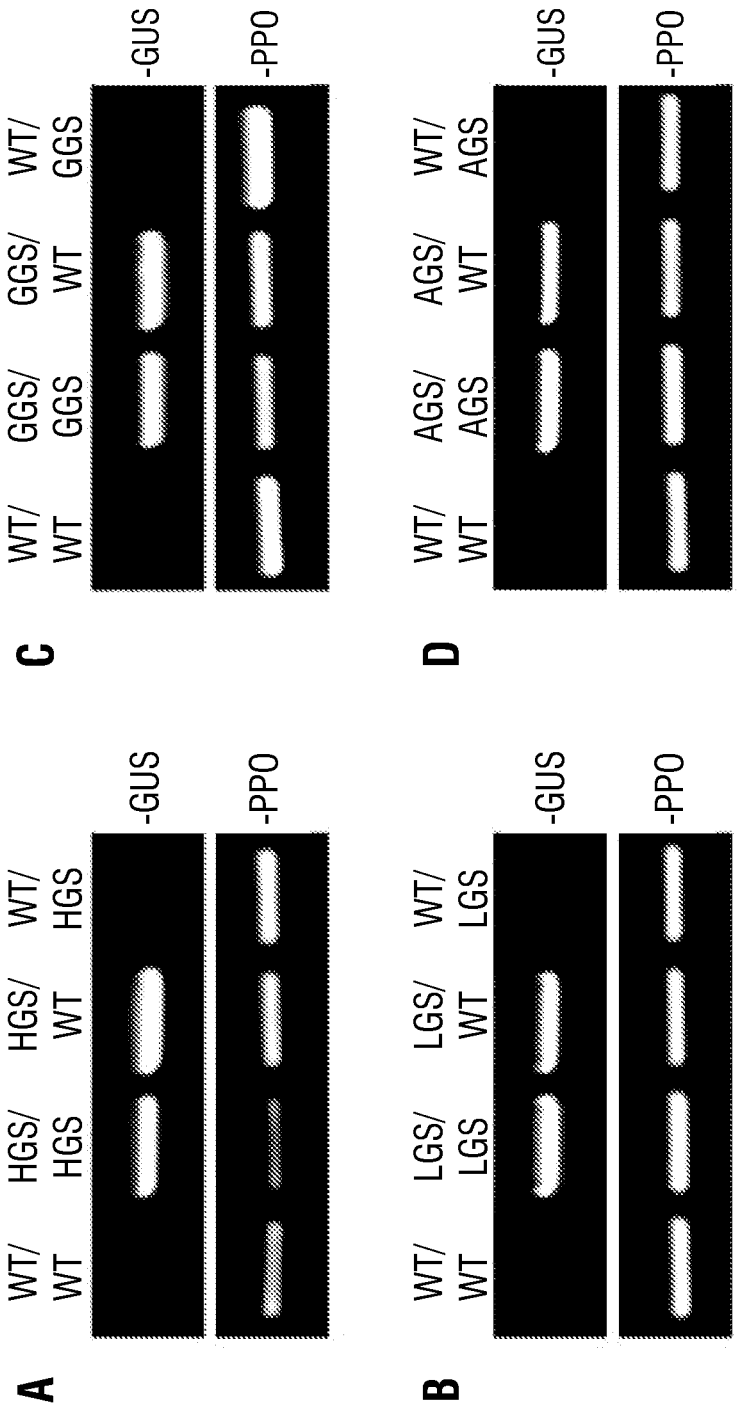
FIG. 9 shows the PCR analysis of the GUS gene in fruiting bodies grown using wild-type and transgenic inoculants from Example 4. Indicated is the upper layer inoculant/lower layer inoculant for the bi-layered cultivation substrate. Wild-type (WT) line; GUS lines carrying the HYPA promoter (HGS), LCC2 promoter (LGS), GPD promoter (GGS), and ACTN promoter (AGS). Shown are the results for lines (A) HGS, (B) LGS, (C) GGS, and (D) AGS. The predicted 163-bp GUS amplicon (GUS) and 403-bp amplicon for the endogenous polyphenol oxidase 1 (PPO) gene, which was included as a PCR control, are indicated.
Figure 10:
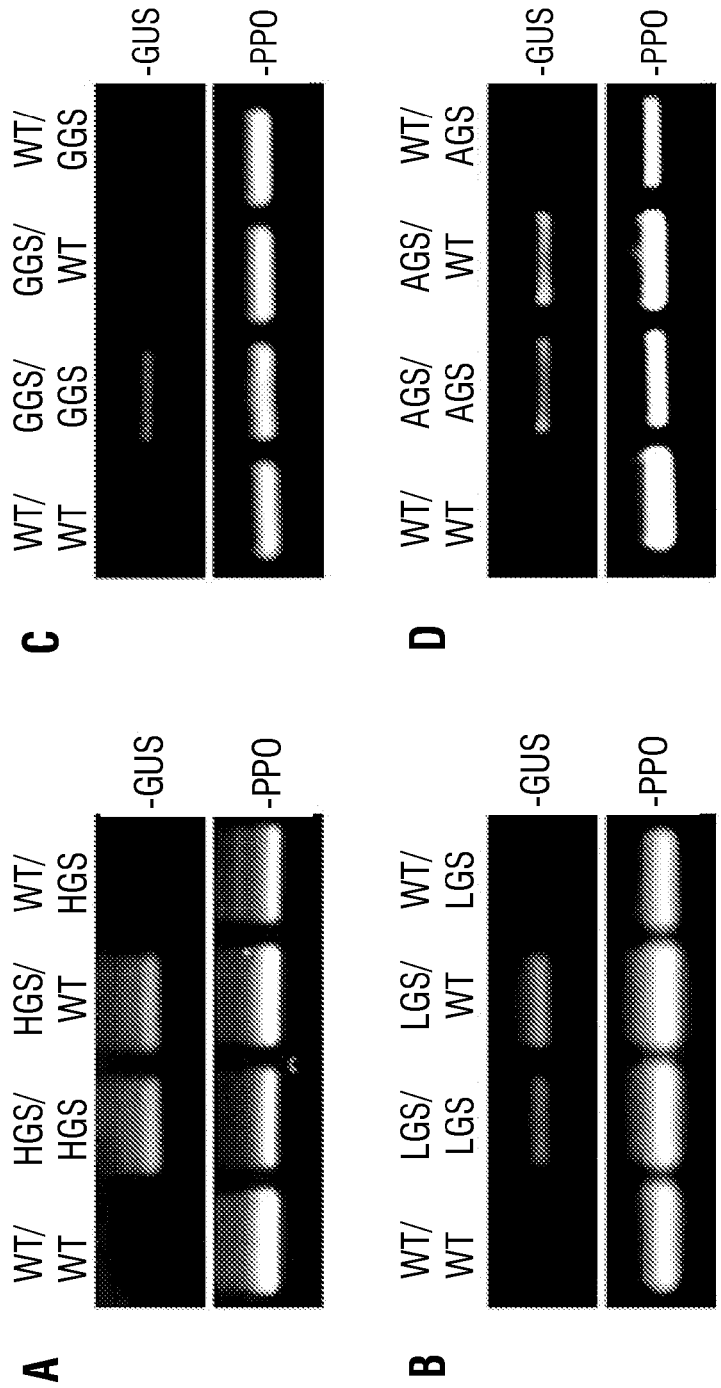
FIG. 10 shows the RT-PCR analysis of the GUS transcript in fruiting bodies grown using wild-type and transgenic inoculants from Example 4. Indicated is the upper layer inoculant/lower layer inoculant for the bi-layered cultivation substrate. Wild-type (WT) line; GUS lines carrying the HYPA promoter (HGS), LCC2 promoter (LGS), GPD promoter (GGS), and ACTN promoter (AGS). Shown are the results for lines (A) HGS, (B) LGS, (C) GGS, and (D) AGS. The predicted 163-bp GUS transcript amplicon (GUS) and 403-bp amplicon for the endogenous polyphenol oxidase 1 (PPO) gene transcript, which was included as a PCR control, are indicated.

To elucidate the relationship between GUS activity and genotype as a function of the spatial position of a transgenic inoculant, fruiting bodies were subjected to PCR and RT-PCR analyses for the GUS gene and RNA transcript, respectively. In all cases, the genotype of the fruiting body was determined solely by the genotype of the inoculant used in the upper layer. The GUS amplicon that was predictive of the GUS gene and mRNA was detected in the fruiting body only when a transgenic inoculant was applied to the upper layer (FIGS. 9 and 10). This finding indicates that the mycelial inoculant in the upper layer gives rise to the fruiting body, largely to the exclusion of the lower-layer inoculant.

While the genotype of the inoculant in the upper layer strictly governed the presence or absence of the GUS gene in the fruiting body, this genotype was not highly predictive of the GUS enzyme activity. Most notably, the WT/LGS, WT/GGS, and WT/AGS combinations produced fruiting bodies showing high GUS activity, but completely lacking the GUS gene and transcript (FIGS. 8-10).

The incongruity between the GUS genotype and phenotype can only be explained if the GUS enzyme was not synthesized in the fruiting body and upper-layer mycelium, but was translocated as either protein or mRNA from the lower-layer mycelium. However, RT-PCR showed that fruiting bodies with high-level GUS activity did not contain the GUS transcript. Thus, the translocated molecule must be GUS protein. Based on this evidence, it was concluded that organogenesis in *A. bisporus* is associated with a highly robust mechanism for the movement of protein from the mycelium colonizing the lower compost layer to the developing fruiting body.

The level of GUS activity expressed by the fruiting body did not correlate well with the presence or absence of the GUS gene. This observation is best exemplified by WT/LGS, WT/GGS, and WT/AGS fruiting bodies, which displayed high-level GUS activity while lacking the GUS gene and transcript. These findings can only be explained by the translocation of GUS protein from the lower-layer mycelium to the fruiting body.

Example 5

Figure 11:
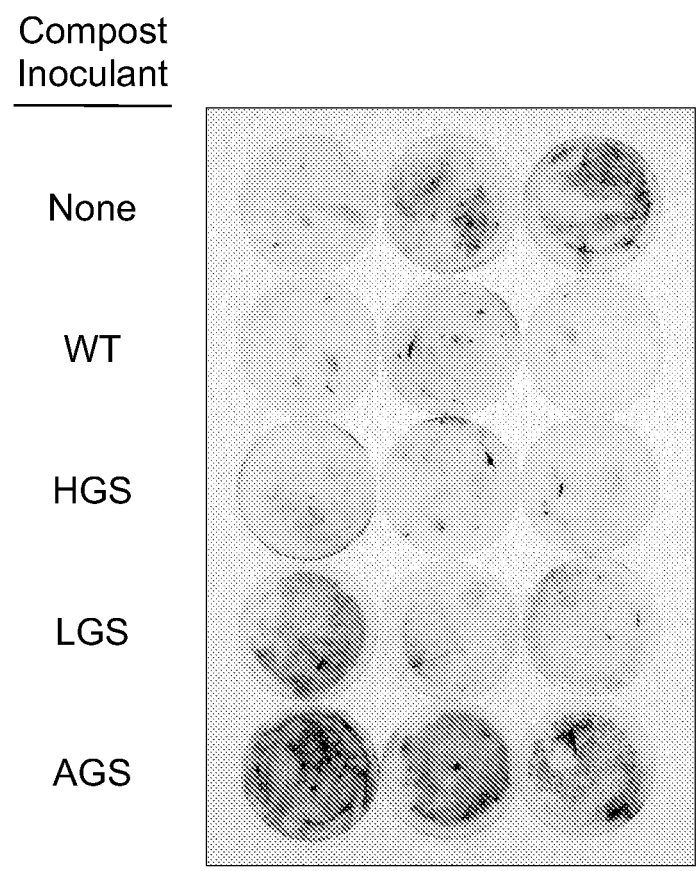
FIG. 11 shows the GUS enzyme activity in the mycelium colonizing the lower-layer compost substrate for different transgenic lines from Example 5. For each line, three paper discs were exposed to the compost during the 14-day mycelial colonization phase in the cropping cycle and then assayed for GUS activity. Compost treatments were: non-inoculated (None); WT-inoculated (WT); inoculated with GUS lines carrying the HYPA (HGS), LCC2 (LGS), and ACTN (AGS) promoters. GUS activity was positively correlated with the predicted activity of the promoter in the vegetative mycelium and with the observed capacity of the particular A. bisporus line to translocate GUS protein from the lower layer to the fruiting body.

In this example, several transgenic lines were characterized for the level of GUS activity expressed by their mycelium colonizing the lower-layer compost. It was found that the variation in the GUS accumulation in fruiting bodies for different transgenic *A. bisporus* lines can be explained by differences in the tissue-specificity of their promoters driving expression of the GUS transgene (FIG. 11). For example, the LCC2 gene is highly expressed in the vegetative mycelium of *A. bisporus* (Perry et al. 1993; Smith et al. 1998). Consequently, in the WT/LGS treatment, the GUS line carrying the mycelial LCC2 promoter in the lower layer supported synthesis of the GUS protein (FIG. 11), which was then translocated to the fruiting body that developed exclusively from the WT mycelium in the upper layer. Inverting the inoculants (LGS/WT) produced fruiting bodies that contained the GUS gene, but showed a markedly diminished GUS activity, because GUS protein was no longer translocated from the WT mycelium in the lower layer.

Alternatively, the HYPA promoter is highly active in the fruiting body, rather than the vegetative mycelium (De Groot et al. 1996) (FIG. 11). Therefore, appreciable GUS activity only resulted when an HGS line was applied to the upper layer, where the fruiting body formed exclusively from its mycelium.

Finally, the combined data from the GUS activity assay of fruiting bodies grown from dual inoculants (FIGS. 8-10) and compost-borne mycelium (FIG. 11) supported the constitutive expression of the ACTN gene in the vegetative and reproductive tissues in *A. bisporus*, which agrees with its behavior in other fungal species (Neveu et al. 2007; Ibrahim et al. 2010). Hence, constitutive expression accounts for why the AGS line produces appreciably GUS activity when paired with a WT inoculant positioned in either the upper or lower layer, because GUS protein was synthesized and translocated from the lower-layer mycelium, and synthesized in situ in the fruiting body as well as in the upper-layer mycelium.

Example 6

Figure 12:
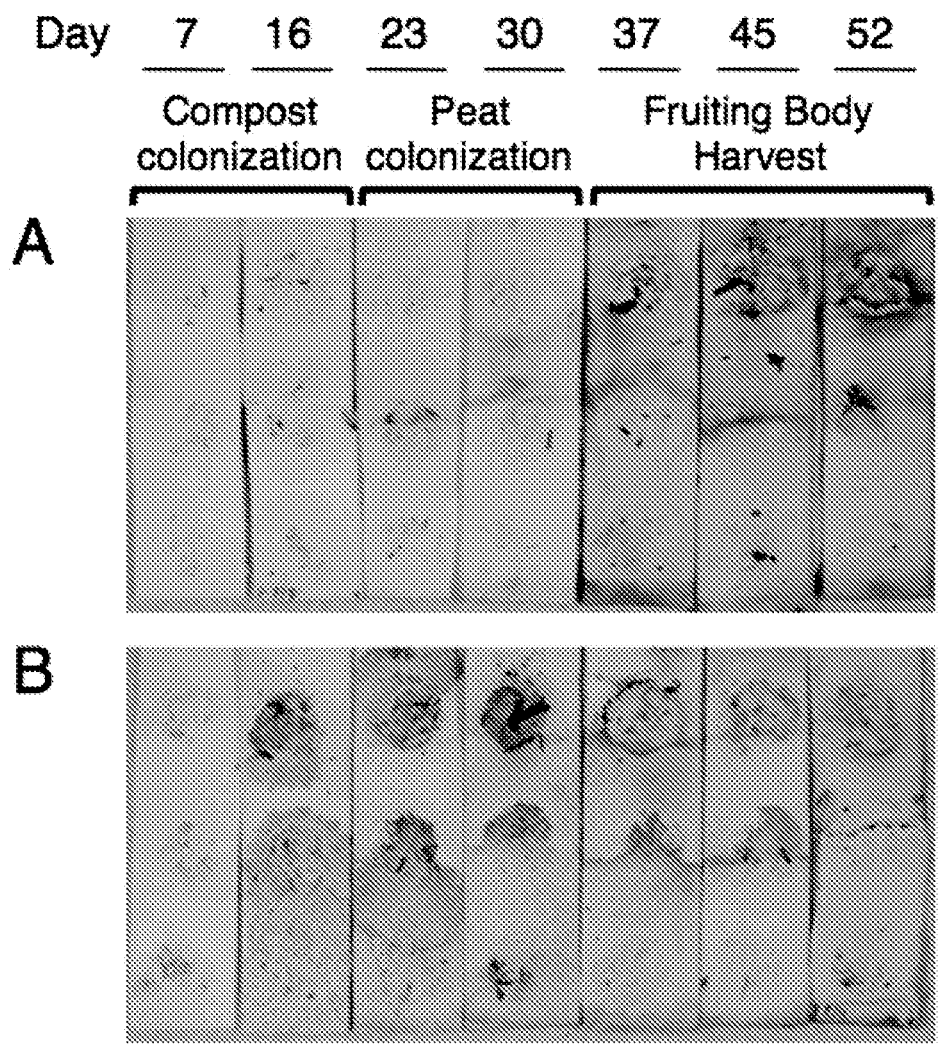
FIG. 12 shows the GUS enzyme activity expressed by the mycelium of A. bisporus colonizing the compost as a function of the time in the cropping cycle from Example 6. A series of three longitudinal 1.75-cm diameter holes spaced 2-cm apart were bored in plastic containers, so as to span the 12-cm depth of the lower compost layer. Each series of three longitudinal holes was covered with a single strip of filter paper. Containers were then filled with either (A) compost or (B) compost inoculated with transgenic line LGS in which the GUS gene was driven by the mycelium-active LCC2 promoter. At various time intervals, a filter paper strip, which was colonized by LGS mycelium, was removed and assayed for GUS activity.

Similar to Example 5, the present study examined changes in the level of GUS activity during the entire 52-day cropping cycle in the mycelium growing in the compost of line LGS, which carries the mycelium-active LCC2 promoter. FIG. 12 illustrates the accumulation of GUS enzyme during a 16-day compost colonization period (Days 7 and 16) and 14-day peat colonization period (Days 23 and 30), and then a steady decline in activity during the fruiting body-harvest period (Days 37, 45, 52). These findings are consistent with the synthesis of the GUS protein in the mycelium during the compost colonization stage and its translocation in to the developing fruiting body.

Example 7

Figure 13:
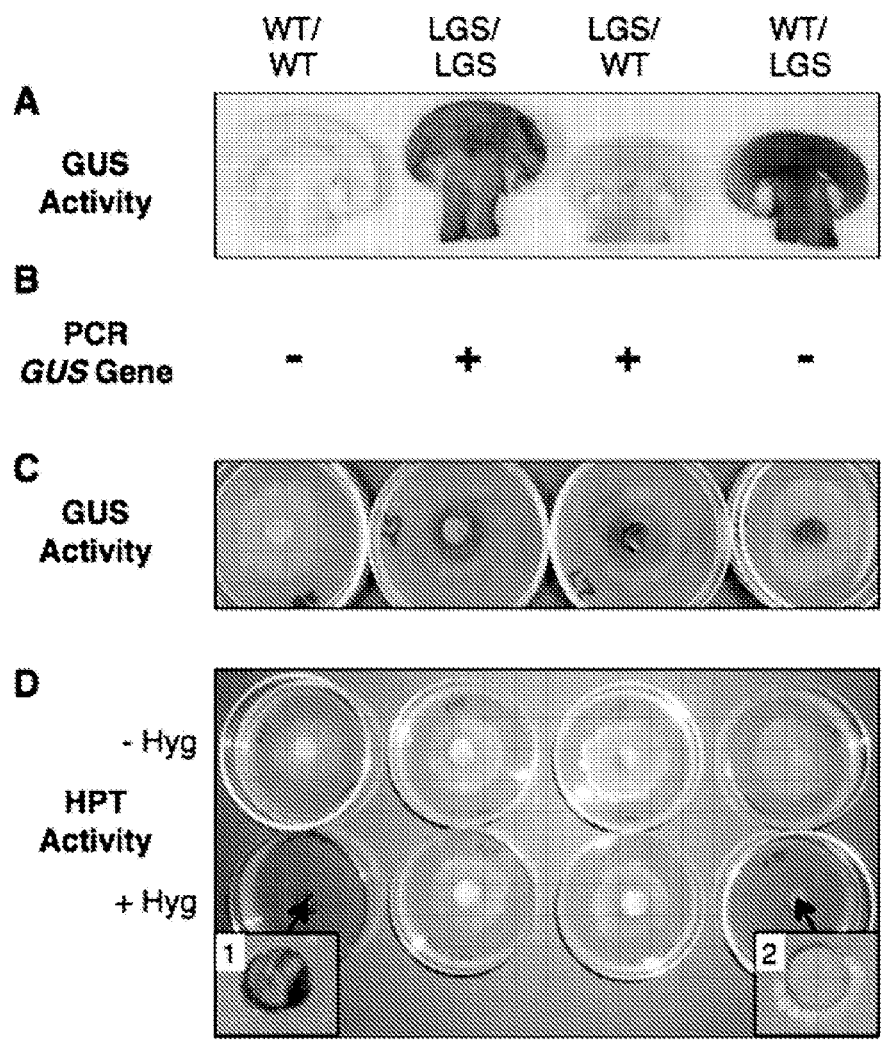
FIG. 13 shows the GUS activity and hygromycin phosphotransferase (HPT) selectable marker activity in mycelium derived from fruiting bodies grown using wild-type and transgenic inoculants from Example 7. Indicated is the upper layer inoculant/lower layer inoculant for the bi-layered cultivation substrate. Wild-type (WT) line; transgenic GUS line carrying the LCC2 promoter (LGS). (A) Histological GUS assay and (B) GUS-PCR analysis of fruiting bodies. The presence (+) or absence (−) of the GUS gene is indicated. Mycelial tissue cultures derived from the fruiting bodies were analyzed for (C) GUS activity by histochemical assay and (D) HPT activity. Hygromycin resistance was assessed by growth on MEA containing hygromycin (+Hyg). Inserts 1, 2: higher magnification of the tissue discs indicated by the arrows.
Figure 14:
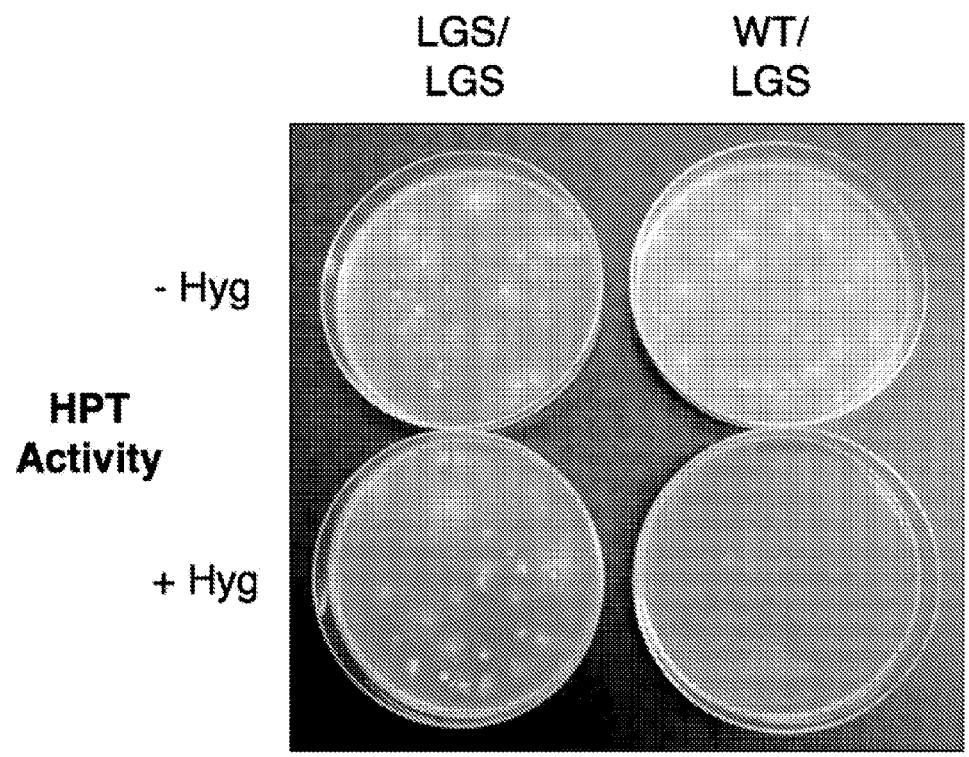
FIG. 14 shows the inheritance of hygromycin phosphotransferase (HPT) selectable marker activity by basidiospores produced by fruiting bodies grown using wild-type and transgenic inoculant from Example 8. Indicated is the upper layer inoculant/lower layer inoculant for the bi-layered cultivation substrate. Wild-type (WT) line; transgenic GUS line carrying the LCC2 promoter (LGS). Hygromycin resistance was assessed by growth on MEA without (−Hyg) and with (+Hyg) hygromycin.

In this study, mycelial cultures derived from the cap tissue of fruiting bodies grown from combinations of WT and LGS lines were assayed for GUS activity and hygromycin phosphotransferase (HPT) selectable maker activity, which confers hygromycin resistance. FIG. 13 demonstrates that the stable expression of GUS and HTP enzyme activities by a mycelial culture was absolutely dependent on the presence of the GUS gene in the fruiting body that was used as a source of the mycelial tissue. Particularly noteworthy was the lack of stable GUS (FIG. 13 C) and HPT (FIG. 13 D) activities in mycelium derived from the WT/LGS fruiting body, which expressed high-level GUS activity, but was completely devoid of the GUS gene (FIG. 13 B). However, the WT/LGS-tissue disc displayed transient hygromycin resistance (FIG. 13 D, insert 2) which was consistent with co-translocation of the HPT and GUS proteins from the lower-layer LGS mycelium. The finding of this study provide confirmatory evidence for the bona fide WT makeup of the WT/LGS-fruiting body. Determination of HPT Activity in Basidiospores and Fruiting Body Tissue.

To screen basidiospores for the co-transformed HPT gene conferring the hygromycin-resistance selection marker, a fruiting body approaching full maturity was soaked in a 10% commercial bleach solution (final concentration 0.6% NaClO) for 1 min, and then rinsed exhaustively with sterile Milli-Q water." Using a scalpel, the stem and veil tissue were excised to expose the lamellae, and the cap was suspended from a hooked wire over a sterilized 9-cm diameter filter paper disc within a sterilized glass chamber. After an overnight incubation, the discharged basidiospores were washed from the surface of the paper with sterile Milli-Q water." A 100-µl aliquot of a turbid basidiospore suspension (>100,000 basidiospores/ml as determined by hemocytometry) was spread onto each of a 10-cm diameter Petri plate of MEA and MEA containing 100 µg/ml hygromycin, and the plates were incubated at room temperature for 3-4 wks.

To assay fruiting body tissue for hygromycin resistance, a 0.5-cm disc of internal cap tissue was transferred aseptically onto each of a 6-cm diameter Petri plate of MEA and MEA containing 50 µg/ml hygromycin. The plates were incubated at room temperature for 2-3 wks.

Example 8

As a corollary to Example 7, the objective of the present study was to examine the inheritance of HPT activity in basidiospores produced by fruiting bodies grown from combinations of WT and LGS lines. In agreement with the findings of Example 7, inheritance of the HPT gene by a basidiospore population, based on the expression of hygromycin resistance, was wholly dependent on the presence of the GUS gene in the fruiting body that served as a source of the basidiospores. Hence, the HPT transgene was not inherited by basidiospores from the WT/LGS-fruiting body that displayed high-level GUS enzyme activity, but was PCR-negative for the GUS gene.

The practical consequences of our findings emphasize the ability to independently manipulate the genotype and phenotype of the fruiting body, which creates the unique opportunity to apply biotechnology for crop improvement. A transgenic line could be employed in the lower layer in the dual-inoculant strategy to enable the translocation of a protein conferring a desirable trait to an otherwise WT fruiting body originating from the upper layer. In addition to the transgene-free status of the edible fruiting body, this strategy would offer the advantage of enhanced biocontainment, as the basidiospores would also be free of the transgene.

Example 9

Figure 15:
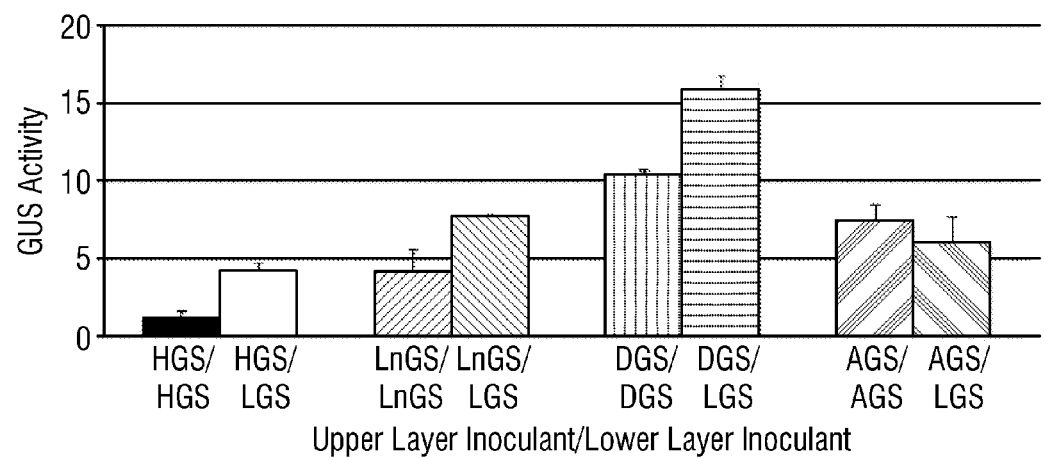
FIG. 15 shows the use of the protein translocation mechanism in A. bisporus to achieve increased recombinant protein production in the fruiting body from Example 9. Shown is GUS activity in fruiting bodies grown using single-transgenic inoculant and dual-transgenic inoculant strategies. Indicated is the upper layer inoculant/lower layer inoculant for the bi-layered cultivation substrate. The single-inoculant treatment employed an A. bisporus line carrying a fruiting body-active promoter as the inoculant for both layers; either HGS (HYPA promoter) LnGS (LCTN promoter), DGS (FBSD promoter), or AGS (ACTN promoter). For the dual-inoculant treatment, lines HGS, LnGS, DGS, and AGS were used as the upper-layer inoculant and individually paired with line LGS carrying the mycelium-active LCC2 promoter as the inoculant for the lower layer. GUS activity is expressed as nmol MUG hydrolyzed/min/100 µg of total soluble protein, and represents the mean value of two independent experiments. GUS activity for inoculant treatment WT/LGS=3.77.
Figure 16:
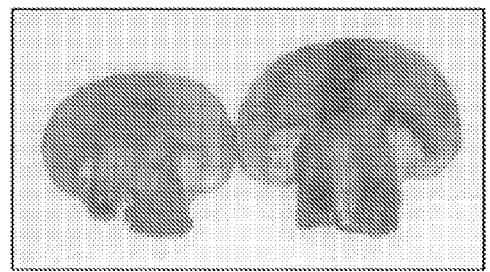
FIG. 16 shows the use of the protein translocation mechanism in A. bisporus to achieve increased recombinant protein production in the fruiting body from Example 9. Shown are the results of a histological assay of GUS activity in fruiting bodies grown using single-transgenic inoculant and dual-transgenic inoculant strategies. Indicated is the upper layer inoculant/lower layer inoculant for the bi-layered cultivation substrates. The single-inoculant treatment used an A. bisporus line carrying a fruiting body-active promoter to seed both layers; either HGS (HYPA promoter) LnGS (LCTN promoter), DGS (FBSD promoter), or AGS (ACTN promoter). For the dual-inoculant treatment, lines HGS, LnGS, DGS, and AGS were used in the upper-layer and individually paired with line LGS carrying the mycelium-active LCC2 promoter in the lower layer.
Figure 16:
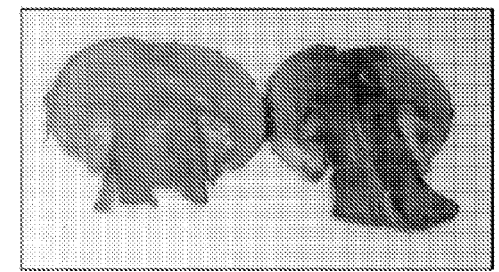
Figure 16:
Figure 16:
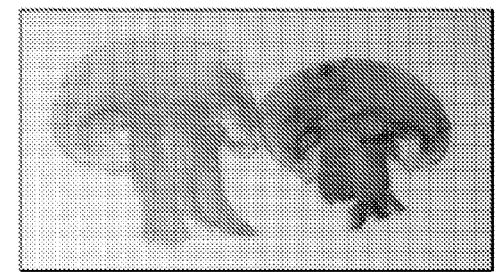

An appreciation for the protein translocation in *A. bisporus* enables the rationale design of transgene constructs with the aim of achieving increased recombinant expression. In the present study, a "spatial gene-stacking" strategy was tested where a higher level of recombinant protein might be attained through the translocation of protein from the lower layer combined with in situ synthesis in the fruiting body. Here, the LGS line, which carries the strong mycelium-active LCC2 promoter, was individually paired with four GUS lines carrying different fruiting body-preferred promoters as the upper-layer inoculants. These lines were HGS (HYPA promoter), AGS (ACTN promoter), DGS (FBSD promoter), and LnGS (LCTN promoter). FIGS. 15 and 16 demonstrate that with the exception of line AGS, a significantly increased GUS activity resulted for each transgenic inoculant pair relative to the level obtained with the single transgenic inoculant. The increase in enzyme activity ranged from 1.5-fold for line DGS to 3.6-fold for line HGS. The increase in GUS activity was not observed with line AGS, because the independent transgenic line representing this GUS construct showed higher enzyme activity than the one representing LGS.

References

Alexopoulos, C. J., C. W. Mims, and M. Blackwell. 1996. Introductory Mycology. John Wiley and Sons, Inc. New York, N.Y. 869 pp.

Beyer, D. M. 2003. Basic procedures for *Agaricus* mushroom growing. College of Agricultural Sciences. Agricultural and Research and Cooperative Extension. The Pennsylvania State University, University Park, Pa. 15 pp.

Bradford, M. M. 1976. Rapid and sensitive method for quantitation of microgram quantities of protein utilizing principle of protein-dye binding. Anal. Biochem. 72:248-254.

Broothaerts W, Mitchell H J, Weir B, Kaines S, Smith L M A, Yang W, Mayer J E, Roa-Rodriguez C, Jefferson R A. 2005. Gene transfer to plants by diverse species of bacteria. Nature 433:629-633.

Callis, J., T. Carpenter, C. W. Sun, and R. D. Vierstra. 1995. Structure and evolution of genes encoding polyubiquitin and ubiquitin-like proteins in *Arabidopsis thaliana* ecotype Columbia. Genetics 139:921-39.

Chen, X., C. P. Romaine, M. D. Ospina-Giraldo, and D. J. Royse. 1999. A PCR-based test for the identification of *Trichoderma harzianum* biotypes 2 and 4 inciting the worldwide green mold epidemic in cultivated *Agaricus bisporus*. Appl. Microbiol. Biotechnol. 52:246-250.

Chen, X., M. Stone, C. Schlagnhaufer, and C. P. Romaine. 2000. A fruiting body tissue method for efficient *Agrobacterium*-mediated transformation of *Agaricus bisporus*. Appl. Environ. Microbiol. 66:4510-4513.

De Groot, P. W. J., P. J. Schaap, A. S. Sonnenberg, J. Visser, and L. J. L. D. Van Griensven. 1996. The *Agaricus bisporus* hypAgene encodes a hydrophobin and specifically accumulates in peel tissue of mushroom caps during fruit body development. J. Mol. Biol. 257:1008-1018.

Harmsen, M. C., F. H. J. Schuren, S. M. Moukha, C. M. van Zuilen, and P. J. Punt. 1992. Sequence analysis of the glyceraldehyde 3-phosphate dehydrogenase genes from the basidiomycetes *Schizophillum commune, Phanerochaete chrysosporium*, and *Agaricus bisporus*. Curr. Genet. 22:447-454.

Ibrahim, A. S. et al. 2010. The high affinity iron permease is a key virulence factor required for *Rhizopus oryzae* pathogenesis. Mol. Microbiol. 77:587-604.

MacCanna, C., and J. B. Flanagan. 1972. Casing types and techniques. Mushroom Sci. 8:727-731.

Neveu, B., M. Michaud, F. Belzile, and R. R. Belanger. 2007. The *Pseudozyma flocculosa* actin promoter allows the strong expression of a recombinant protein in the *Pseudozyma* species. Appl. Microbiol. Biotechnol. 74:1300-1307.

O'Neill, K. A., J. S. Larsen, and W. R. Curtis. 2008. Scale-up of *Agrobacterium*-mediated transient protein expression in bioreactor-grown *Nicotiana glutinosa* plant cell suspension culture. Biotechnol. Prog. 24:372-376.

Penn State Handbook for Commercial Mushroom Growers. 1982. P. J. Wuest and G. D. Bengtson (eds.). The Pennsylvania State University. University Park, Pa. 129 pp.

Perry C. R., M. Smith, C. H. Britnell, D. A. Wood, and C. F. Thurston. 1993. Identification of two laccase genes in the cultivated mushroom *Agaricus bisporus*. J. Gen. Microbiol. 139: 1209-1218.

Romaine, C. P. and X. Chen. 2005. Methods and compositions for highly efficient transformation of filamentous fungi. U.S. Pat. No. 6,964,866.

Romaine, C. P. and X. Chen 2009. Methods and compositions for highly efficient transformation of filamentous fungi. U.S. Pat. No. 7,700,349.

Romaine, C. P. and B. Schlagnhaufer. 1992. Characteristics of a hydrated alginate-based delivery system for cultivation of the button mushroom. Appl. Environ. Microbol. 58:3060-3066.

Romaine, C. P. and C. Schlagnhaufer. 2006. Mushroom (*Agaricus bisporus*). In: *Agrobacterium* Protocols, Vol. 2, pp. 453-463. K. Wang (ed.). Methods in Molecular Biology 344. Humana Press Inc.

Smith, M., A. Shnyreva, D. A. Wood, and C. F. Thurston. 1998. Tandem organization and highly disparate expression of the two laccase genes lcc1 and lcc2 in the cultivated mushroom *Agaricus bisporus*. Microbiol. 144:1063-1069.

Wichers, H. J. et al. 2003. Cloning, expression and characterization of two tyrosinase cDNAs from *Agaricus bisporus*. Appl. Microbiol. Biotechnol. 61:336-341.

What is claimed is:

1. A method of producing a filamentous fungus fruiting body to confer an altered phenotype, but a wild-type genotype comprising:
    seeding a lower nutrient substrate layer with a first filamentous fungal mycelial inoculant, so that said substrate becomes colonized with the mycelial inoculant,
    overlaying said lower nutrient substrate layer with an upper water-holding substrate layer that has been inoculated with a second transgenic filamentous fungal mycelial inoculant, wherein said second transgenic filamentous fungal mycelial inoculant incorporates a heterologous polynucleotide construct, and
    allowing fruiting bodies to form, wherein said formed fruiting bodies include the heterologous polynucleotide product from the second transgenic filamentous fungal mycelial inoculant.

2. The method of claim 1 wherein said second transgenic inoculant has a heterologous expression construct.

3. The method of claim 2 wherein said expression construct encoding an agronomic, industrial, or therapeutic protein.

4. The method of claim 2 wherein said heterologous polynucleotide construct is an inhibition construct.

5. The method of claim 1 wherein said first filamentous fungal mycelial inoculant is a transgenic filamentous fungus incorporating a heterologous polynucleotide construct.

6. The method of claim 5 wherein said first inoculant polynucleotide construct comprises a polynucleotide sequence encoding a heterologous protein operably linked to a promoter that expresses preferentially in vegetative mycelium.

7. The method of claim 6, wherein said promoter is selected from the group consisting of glyceraldehyde 3-phosphate dehydrogenase promoter, and the laccase 2 promoter.

8. The method of claim 2 wherein said second filamentous fungal inoculant polynucleotide construct comprises a polynucleotide sequence encoding a heterologous protein operably linked to a promoter sequence that expresses preferentially in the fruiting body.

9. The method of claim 6 wherein said promoter is HYPA.

10. A method of modulating the activity of an endogenous or heterologous protein in a fruiting body of a filamentous fungus comprising:
    seeding a lower nutrient substrate layer with a first transgenic filamentous fungal mycelial inoculant, so that said substrate becomes colonized with the mycelial inoculant,
    wherein said first transgenic filamentous fungal mycelial inoculant incorporates a heterologous polynucleotide construct,
    overlaying said nutrient substrate with an upper water-holding substrate layer that has been inoculated with a second non-transgenic filamentous fungal mycelial inoculant, and
    allowing fruiting bodies to form, wherein the polynucleotide construct from the first transgenic filamentous fungal inoculant construct provides modulation of an endogenous protein or heterologous protein in the formed fruiting bodies.

11. The method of claim 5 wherein said second inoculant is wild-type.

12. The method of claim 10 wherein said heterologous protein construct is an expression construct with a polynucleotide sequence encoding a protein operably linked to a promoter active in a fungal cell.

13. The method of claim 12 wherein said protein is present n said fruiting bodies, but the polynucleotide construct is not.

14. The method of claim 10 wherein said heterologous polynucleotide construct is an inhibition construct with an inhibition sequence operably linked to a promoter active in a fungal cell.

15. The method of claim 12 wherein said protein is modulated in fruiting bodies, but the inhibition construct is not present.

16. A method for transgenic manipulation of a filamentous fungus comprising:
    inoculating said fungus in an upper cultivation substrate wherein said inoculant is with a genotype desired in a fruiting body, and
    inoculating a lower cultivation substrate with a fungus that comprises an RNA and/or protein desired in said resulting fruiting body.

17. The method of claim 16 wherein said upper inoculant is non-transgenic type so that a wild-type genotype is conferred to the fruiting body and further wherein the lower compost inoculant is transgenic and protein/mRNA is shuttled up into the wild-type fruiting body.

18. A method of producing a fruiting body that includes the genotype of one inoculant, and the phenotype of a second inoculant comprising:
    seeding a lower nutrient substrate layer with a first filamentous fungal mycelial inoculant, so that said substrate becomes colonized with the mycelial inoculant, the phenotype of said first inoculant being one that is desired in a produced fruiting body,
    overlaying said lower nutrient substrate layer with an upper water-holding substrate layer that has been inoculated with a second filamentous fungal mycelial inoculant, the genotype of said second inoculant being one which is desired in said produced fruiting body; and
    allowing fruiting bodies to form, wherein said formed fruiting bodies include the genotype of the second inoculant and the phenotype of the first inoculant.

19. The method of claim 18 wherein said first inoculant includes a desirable vegetative trait.

20. The method of claim 19 wherein said desired vegetative trait is selected from the group consisting of: capacity for alternative compost nutrient utilization, compost colonization, thermal tolerance, resistance to fungal pathogens, resistance to fungal disease.

21. The method of claim 18 wherein said second inoculant includes a commercially desirable trait the presence of which is desired in the fruiting body.

22. The method of claim 21 wherein said commercially desirable trait is the production of a heterologous protein.

23. A method for producing fruiting bodies of a filamentous fungus comprising:
    seeding a lower nutrient substrate layer with a transgenic mycelial inoculant, so that said substrate becomes colonized by the mycelial inoculant, and either
    overlaying said lower nutrient substrate with an upper water-holding substrate layer that has been seeded with the same transgenic mycelial inoculant used in the lower substrate layer or
    overlaying said lower nutrient substrate with an upper water-holding substrate layer that has not been seeded with a mycelial inoculant, but rather is allowed to become colonized by the transgenic mycelial inoculant used in the lower substrate layer, and
    allowing fruiting bodies to form, wherein said formed fruiting bodies possess a recombinant protein from the transgenic mycelial inoculant.

24. The method of claim 23 where the transgenic mycelial inoculant includes a polynucleotide construct that encodes a heterologous protein operably linked to a promoter that expresses in the vegetative mycelium and fruiting body.

25. The method of claim 24 wherein the polynucleotide construct includes a second promoter, one that is highly active in the vegetative mycelium and the other in the fruiting body.

26. The method of claim 23 where the transgenic mycelial inoculant carries multiple copies of polynucleotide construct operably linked to one or more promoters that are either highly active in the vegetative mycelium or fruiting body or are highly active in the vegetative mycelium and fruiting body.

* * * * *

UNITED STATES PATENT AND TRADEMARK OFFICE
CERTIFICATE OF CORRECTION

Page 1 of 1

PATENT NO. : 8,686,218 B2
APPLICATION NO. : 13/640131
DATED : April 1, 2014
INVENTOR(S) : Romaine et al.

It is certified that error appears in the above-identified patent and that said Letters Patent is hereby corrected as shown below:

In the Claims

Col. 43, Claim 13, Line 66:
DELETE before said "n"
ADD before said --in--

Signed and Sealed this
Tenth Day of June, 2014

Michelle K. Lee
*Deputy Director of the United States Patent and Trademark Office*